United States Patent
Corley et al.

(10) Patent No.: US 10,470,667 B2
(45) Date of Patent: Nov. 12, 2019

(54) SYSTEM FOR MANAGEMENT AND PREVENTION OF VENOUS POOLING

(71) Applicants: NATIONAL UNIVERSITY OF IRELAND, GALWAY, Galway (IE); UNIVERSITY OF LIMERICK, Limerick (IE)

(72) Inventors: Gavin Corley, Ennis (IE); Gearóid Ó'Laighin, Ennis (IE); Paul Breen, Emly (IE); Barry Broderick, O'Briens Bridge (IE); Pierce A. Grace, Patrickswell (IE); Derek O'Keeffe, Limerick (IE)

(73) Assignees: University of Ireland, Galway, Galway (IE); University of Limerick, Limerick (IE)

( * ) Notice: Subject to any disclaimer, the term of this patent is extended or adjusted under 35 U.S.C. 154(b) by 630 days.

(21) Appl. No.: 14/357,181

(22) PCT Filed: Nov. 9, 2012

(86) PCT No.: PCT/IE2012/000047
§ 371 (c)(1),
(2) Date: May 8, 2014

(87) PCT Pub. No.: WO2013/069002
PCT Pub. Date: May 16, 2013

(65) Prior Publication Data
US 2014/0303460 A1  Oct. 9, 2014

(30) Foreign Application Priority Data

Nov. 11, 2011 (IE) .................................. 2011/0494

(51) Int. Cl.
*A61B 5/0205* (2006.01)
*A61B 5/00* (2006.01)
(Continued)

(52) U.S. Cl.
CPC ............ *A61B 5/0205* (2013.01); *A61B 5/021* (2013.01); *A61B 5/02007* (2013.01);
(Continued)

(58) Field of Classification Search
CPC . A61B 5/6828; A61B 5/6829; A61B 5/02007; A61B 5/021; A61B 5/1071;
(Continued)

(56) References Cited

U.S. PATENT DOCUMENTS 4,494,550 A    1/1985  Blazek et al.
5,919,141 A *  7/1999  Money ............... A61B 5/02055
                                                    600/483
(Continued)

FOREIGN PATENT DOCUMENTS

EP    1254629 A1    11/2002
WO    20001006076 A1    2/2000
(Continued)

OTHER PUBLICATIONS

Meissner et al. "Chapter 1—The hemodynamics and diagnosis of venous disease" Journal of Vascular Surgery vol. 46, Issue 6, Supplement, Dec. 2007, pp. S4-S24.*
(Continued)

*Primary Examiner* — Nathan J Jenness
(74) *Attorney, Agent, or Firm* — Studebaker & Brackett PC

(57) ABSTRACT

A monitoring system comprises sensors adapted to be worn by a user, and, a processor linked with the sensor. The processor receives sensor data and processes this data to determine user posture data including data indicative of vertical distance between level of the user's heart and ankle. Based on the posture data together with a value for degree of user chronic venous insufficiency and/or blood density, generate an estimate of user static venous pressure while the
(Continued)

user is static, without calf muscle pump activity. The processor also processes the sensor data to determine if there is calf muscle pump activity, and generates an estimate of user active venous pressure according to the static venous pressure estimate, rate of calf muscle activity, and a value for degree of user chronic venous insufficiency. The processor may generate the venous pressure estimate in real time, and may control an NMES device accordingly.

10 Claims, 16 Drawing Sheets

(51) Int. Cl.
| | |
|---|---|
| *A61B 5/02* | (2006.01) |
| *A61B 5/021* | (2006.01) |
| *A61B 5/107* | (2006.01) |
| *A61B 5/11* | (2006.01) |
| *A61N 1/36* | (2006.01) |
| *A61B 5/0295* | (2006.01) |

(52) U.S. Cl.
CPC .......... *A61B 5/0295* (2013.01); *A61B 5/1071* (2013.01); *A61B 5/1072* (2013.01); *A61B 5/1116* (2013.01); *A61B 5/1118* (2013.01); *A61B 5/6828* (2013.01); *A61B 5/6829* (2013.01); *A61B 5/746* (2013.01); *A61N 1/36003* (2013.01); *A61B 5/4836* (2013.01); *A61B 5/6823* (2013.01); *A61N 1/36135* (2013.01)

(58) Field of Classification Search
CPC ... A61B 5/1072; A61B 5/1116; A61B 5/0205; A61B 5/0295; A61B 5/1118; A61B 5/746
See application file for complete search history.

(56) References Cited

U.S. PATENT DOCUMENTS

| | | | | |
|---|---|---|---|---|
| 6,432,061 | B1* | 8/2002 | Nissila | A61B 5/02152 600/485 |
| 2007/0167844 | A1* | 7/2007 | Asada | A61B 5/022 600/485 |
| 2008/0077026 | A1* | 3/2008 | Banet | A61B 5/02055 600/509 |
| 2008/0306354 | A1 | 12/2008 | Mason | |
| 2009/0048525 | A1* | 2/2009 | Rogers | A61B 5/02007 600/504 |
| 2010/0049096 | A1* | 2/2010 | Ten Kate | G08B 21/0446 600/595 |
| 2010/0125212 | A1 | 5/2010 | Kim et al. | |
| 2010/0179439 | A1 | 7/2010 | Kuschel et al. | |
| 2011/0082517 | A1 | 4/2011 | Brezel et al. | |
| 2011/0190675 | A1* | 8/2011 | Vess | A61H 9/0092 601/152 |

FOREIGN PATENT DOCUMENTS

| | | |
|---|---|---|
| WO | 20071060560 A1 | 5/2007 |
| WO | 2009/150652 A1 | 12/2009 |

OTHER PUBLICATIONS

Nicolaides, A.N. et al. "Photoplethysmography in the assessment of venous insufficiency"Journal of Vascular Surgery , vol. 5 , Issue 3 , 405-412.*

International Preliminary Report on Patentability; PCT/IE2012/000047; dated May 13, 2014.

International Search Report; PCT/EI2012/000047; dated Feb. 21, 2013.

Kugler, Christian et al; "Venous Pressure Dynamics of the Healthy Human Leg: Role of Muscle Activity, Joint Mobility and Anthropometric Factors"; J. Vasc. Res; 2001; vol. 38; pp. 20-29.

Pollack, Albert A. et al.; "The Effect of Exercise and Body Position on the Venous Pressure at the Ankle in Patients Having Venous Valvular Defects"; Divisions of Medicine, Postoperative Care and Physiology, Mayo Foundation, Mayo Clinic, Rochester, MN; Dec. 4, 1948; pp. 559-563.

Eifell, Ron K.G. et al.; "Comparison of New Continuous Measurements of Ambulatory Venous Pressure (AVP) with Conventional Tiptoe Exercise Ambulatory AVP in Relation to the CEAP Clinical Classification of Chronic Venous Disease"; Journal of Vascular Surgery; Oct. 2006; vol. 44, No. 4; pp. 794-803.

* cited by examiner

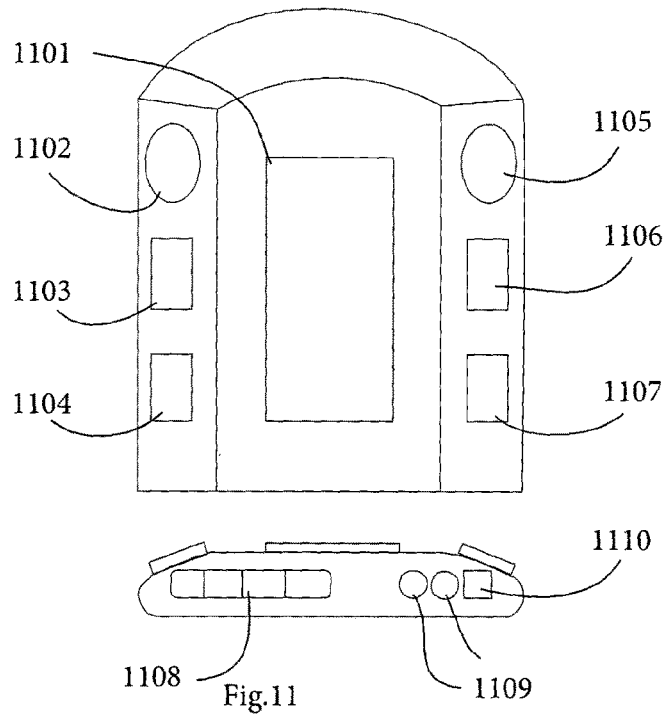
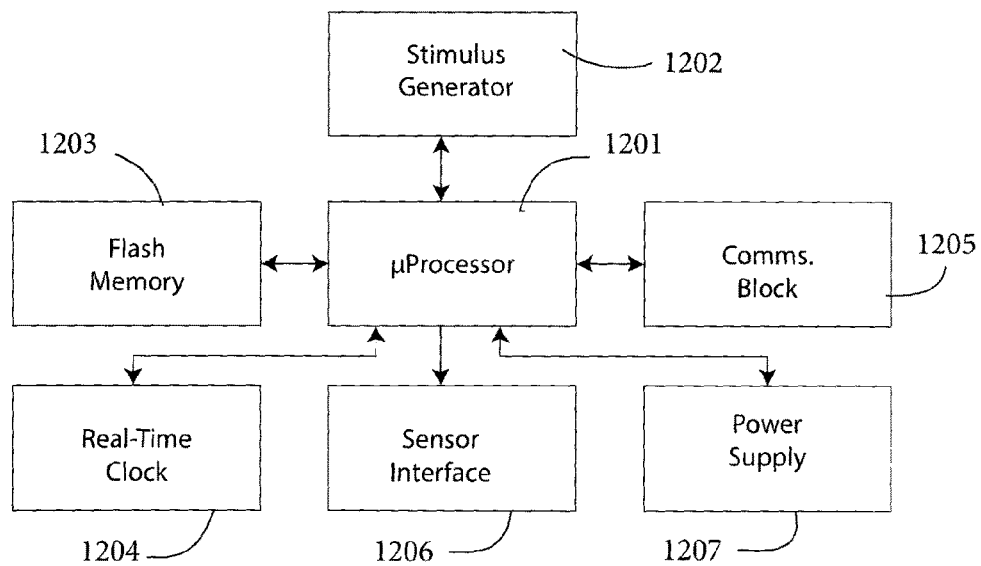
Fig.12

SYSTEM FOR MANAGEMENT AND PREVENTION OF VENOUS POOLING

INTRODUCTION

Field of the Invention

The invention relates to artificial stimulation of flow from the leg and foot and specifically to its application for the prevention and treatment of chronic venous insufficiency ("CVI").

Prior Art Discussion

In the healthy lower leg, blood flow in the veins must typically work against gravity to return to the heart. This unidirectional flow is facilitated by the presence of two mechanisms: venous valves and the calf muscle pump. Venous valves are located throughout the veins and maintain unidirectional flow towards the heart. During contraction, the calf muscles eject blood through the veins and back towards the heart. Both correctly functioning valves and healthy calf muscle pump function are essential for maintaining healthy venous flow and avoiding venous pooling.

Pooling of venous blood in the lower leg is a major contributory factor in the development of chronic venous insufficiency (CVI) which can result from breakdown of the venous valves and/or poor calf muscle pump function. It leads to blood pooling in the veins resulting in increased venous pressure. These pressures are highest during standing and lowest when lying due to the effect of gravity. This increased pressure results in: pain, swelling, oedema, skin changes, varicose veins, deep vein thrombosis and venous leg ulcers. Venous leg ulcers are the most severe and costly manifestation of CVI and are an enormous problem for both patients and healthcare providers.

Circumstances that predispose a person to prolonged venous pooling and the resultant conditions of CVI are:
  Occupational—work posture that requires long periods of sitting or standing (shopkeepers, barmen, hairdressers, pilots, computer programmer).
  Patients—during surgery, during recovery, patients with leg casts.
  Older persons—inactivity, chronic disease and chronic vascular disorders.
  Muscle paralysis—wheelchair bound patients, stroke patients, multiple sclerosis.

Currently, a common treatment for varicose veins and venous leg ulcers is graduated compression therapy. Compression stockings are the most common form of compression therapy and are typically prescribed for the prevention of varicose veins and deep vein thrombosis ("DVT") and for the prevention of the recurrence of venous ulcers. Graduated compression stockings have been shown to reduce the incidence of DVT and are believed to alleviate some of the symptoms of varicose veins. However, compression hosiery is limited by poor compliance and has not been demonstrated to slow the progression of varicose veins.

Graduated compression bandaging is typically used for the most severe symptoms of CVI such as oedema and venous leg ulceration. Graduated compression bandaging consists of several layers of tightly wrapped bandages which exert an inward force on the leg, helping to close venous valves and to counteract the harmful venous pressures in the leg. Despite being the current gold standard treatment for venous leg ulcer care, this treatment modality doesn't allow the clinician to fully address the underlying cause of venous leg ulcers—blood pooling.

Individuals who are predisposed to prolonged venous pooling and CVI currently have very limited options to prevent the progression of symptoms of CVI. Furthermore, clinicians treating this condition are not able to closely monitor the status of venous pooling in these patients and the treatment regimen is based on changes in the severity of the symptoms of this pooling—swelling and ulceration. Consequently it is desirable to monitor and report the status of venous pooling in these patients and apply an intervention for reducing this pooling where possible so that the worsening of symptoms of CVI such as varicose veins and venous leg ulcers may be prevented.

NMES Blood Flow Stimulation:

If prolonged venous pooling is detected it would be desirable to intervene to reduce the pooling. The lower leg muscles act as a natural muscle pump which helps to eject venous blood from the lower leg. Voluntary activity such as walking naturally activates and conditions this muscle pump. However, CVI patients are typically unable to maintain healthy muscle pump function, due to a sedentary lifestyle and exercise is often painful. Therefore an alternative means for activating this muscle pump or rehabilitating it is desirable in these patients.

Neuromuscular electrical stimulation (NMES) is the application of electrical stimuli to a muscle or nerve resulting in a stimulated muscle contraction. Application of NMES to the lower leg muscles has been shown to result in artificial activation of the calf muscle and has been shown to promote venous outflow from the leg and promote muscle strengthening. NMES can be applied via surface electrodes placed over a nerve or muscle on the user's leg (surface NMES) or using implanted micro-stimulators within the patient's leg (implanted NMES).

Surface NMES devices exist today for the treatment of a range of conditions. Several investigators have assessed the use of NMES of the leg muscles for the promotion of venous blood flow through the leg veins and arteries. WO2009/150652, U.S. Pat. No. 5,707,400, WO2007/135667, WO1999/55413, WO2000/006076 describe both NMES or combined NMES and pneumatic systems for the promotion of venous blood flow using stimulation of human limb muscles.

Implanted NMES:

Implanted NMES can be delivered through the use of an implanted micro-stimulator which delivers a stimulus to surrounding tissue. If the micro-stimulator is placed adjacent to a nerve it can stimulate an action potential in that nerve, resulting in muscular contraction. Alternatively direct stimulation of the nerve may be achieved through the use of a stimulating cuff electrode which is placed around the target nerve. Stimulus is generated in an implanted device, and is delivered to the cuff electrodes via implanted wires. An advantage of this approach is that the stimulus generation circuitry does not need to be placed adjacent to the nerve. In both cases, radio-frequency (RF) signals can be used to communicate with the implanted devices, facilitating transmission of data to and from the devices and also allowing for charging of the implanted devices.

Currently, implanted NMES devices require a large cuff to be placed around the limb of interest to facilitate RF transmission to the implanted devices via inductive coupling. These cuffs are bulky and difficult to apply and consequently they may not be suitable for long term use such as CVI prevention.

Compliance Monitors

In the management of CVI patient compliance to a treatment program which encourages lower limb compression and reduction of venous pooling and increased muscle pump activity is significant for effectively implementing the therapy. Furthermore goal setting and feedback for the patients may help to motivate and improve patient compliance to the therapy as well as inform their carer's decision-making process in relation to their treatment. Several disclosures relate to the monitoring of patient compliance to a prescribed treatment or exercise protocol. U.S. Pat. No. 5,800,458 describes an external system to monitor usage of existing electrotherapy devices by monitoring applied current. WO2002/018019 describes a method for monitoring usage of exercise devices for good practice and home-based rehabilitation, while WO2001/087150 describes a generic compliance monitoring system consisting of the sensing of electrical signals using a microprocessor, a docking station type recharging and transmission device and a database for Web-based access to patient data. WO2008/003920 A1 describes a method and apparatus, including a compliance monitor, for monitoring external physical parameters having an influence on the onset or progression of a medical condition.

Breen, Paul P et al: "A programmable and portable NMES device for drop foot correction and blood flow assist applications" Medical Engineering & Physics, Butterworth-Heinemann, G B, vol. 31, no. 3, 1 Apr. 2009 (2009-04-01), pages 400-408, describes an NMES which accepts a variety of sensor inputs, including accelerometer signals. A processor uses accelerometer signals to identify periods of inactivity and modulates stimulation based on this.

GB2439750 (Wound Solutions Ltd.) describes a system which monitors a limb wound, and includes motion and inclination sensors.

US2009/0234262 (Reid, J R et al) describes a health monitoring system with sensors for parameters such as skin temperature, muscle activity, and body motion. An aspect is sensing of edema by means of electrical impedance measurements.

WO2011/075769 (Impedimed Ltd.) describes use of impedance plethysmography to monitor body fluid changes over time.

JP06285046 (Res. Dev. Corp. of Japan) describes use of kinematic sensors such as inclination angle sensors for monitoring patient activity.

The invention is directed towards providing improved management and prevention of venous pooling.

SUMMARY OF THE INVENTION

According to the invention there is provided a monitoring system comprising:
  at least one sensor adapted to be worn by a user, and,
  a processor linked with the sensor,
    wherein the processor is adapted to:
    receive sensor data and process said sensor data to determine user posture data including data indicative of vertical distance between level of the user's heart and ankle, and
    based on said posture data together with a value for degree of user chronic venous insufficiency and/or blood density, generate an estimate of user static venous pressure while the user is static, without calf muscle pump activity.

In one embodiment, the processor is adapted to process said sensor data to determine if there is calf muscle pump activity, and to generate an estimate of user active venous pressure according to said static venous pressure estimate, rate of calf muscle activity, and a value for degree of user chronic venous insufficiency.

In one embodiment, the processor is adapted to estimate the rate of calf muscle activity from rapid changes in acceleration caused by impact forces during impact of the user's heel during calf muscle activity.

In one embodiment, the processor is adapted to generate said venous pressure estimate in real time.

In one embodiment, the processor is adapted to log the sensor data in real time and to subsequently generate the estimate.

In another embodiment, at least one sensor is adapted to detect walking, lying, sitting, and/or standing posture events, and wherein the posture data includes:
  (a) the angle ($\theta 2$) made by the thigh with a reference axis A,
  (b) the angle ($\theta 1$) made by the shank of the leg with a reference axis B.
  (c) any angle between the reference axes A and B
  wherein the vertical distance ($\Delta h$) between the level of the heart and the ankle is calculated using the length of the thigh (L1), the length of the shank of the leg (L2), the distance from the hip to the level of the heart (Vd1), and the joint angles at the hip ($\theta 2$) and the knee ($\theta 1$) using determined postural data.

In one embodiment, the processor is adapted to determine a refill time for a patient using indirect measurement of their venous haemodynamics using air-plethysmography, or direct venous pressure measurements, or estimated measurements based on degree of chronic venous insufficiency, and said refill time is configured into the processor or is automatically selected by the processor from a list of standard values.

In one embodiment, the processor is adapted to process interval time data to determine if an interval being analyzed is less than a refill time, and/or if a postural change occurred during that interval, and/or estimate the average pressure during that interval using estimates of static venous pressures, the duration of the interval, and the venous refill rate.

In one embodiment, the processor is adapted to identify lower leg activity primary phases including an emptying phase, and a plateau phase in which the veins do not empty any further and active venous pressure is maintained at a depressed level. In one embodiment, the processor is adapted to determine a value for mean slope of the active venous pressure change in the emptying phase by the rate of muscle activation and ankle range of motion, and to determine minimal pressure in the plateau phase by the degree of chronic venous insufficiency, calf circumference, ankle range of motion and head change.

In one embodiment, the processor is adapted to communicate the venous pressure data to one or more external devices.

In one embodiment, the system comprises a neuromuscular electrical stimulation (NMES) device, and the processor is adapted to activate said NMES device according to the estimated venous pressure.

In one embodiment, the system comprises at least one RF transmission coil adapted to be mounted on a fixed or mobile object such as a wall or furniture in order to perform ambient activation of the NMES device. In one embodiment, the RF transmission coil is adapted to be mounted in a chair.

In one embodiment, the processor is adapted to control the NMES device in order to minimize venous pooling.

Preferably, the processor is adapted to determine or select NMES device parameters according to at least one of: a venous pressure estimate, a venous pressure-time integral, physical activity levels, leg elevation levels, NMES device usage statistics. In one embodiment, the processor is adapted to generate or select NMES device stimulation parameters including at least one of: stimulation amplitude; pulse width; frequency; stimulation envelope ramp-up, ramp-down, on and off times; number of channels and stimulation schedule. In one embodiment, the NMES device is arranged to stimulate both the posterior and anterior muscle groups of the lower leg. In a further embodiment, at least some NMES devices are arranged to apply stimulation to the peroneal nerve. In one embodiment, the NMES device includes an output stage having a 3-way H-bridge circuit.

In one embodiment, the sensor is wirelessly linked with the processor.

In one embodiment, at least one sensor is adapted to measure the acceleration and tilt of a limb segment in one or more axes.

In another embodiment, the processor is adapted to provide feedback to the user when a predefined time threshold has been reached, the feedback comprising at least one of auditory, visual, or tactile alerts. Preferably, the time threshold is determined by at least one of the following inputs: venous refill time, posture, and activity levels.

In one embodiment, at least one sensor is adapted to provide sensor data indicating step counts and postural transitions, and the processor is adapted to process said data to estimate rate of calf muscle activity in an algorithm for estimating active venous pressure.

In one embodiment, the system includes a docking station for recharging an NMES device and/or a sensor.

In one embodiment, the processor is at least partly incorporated into a housing of the sensor.

In one embodiment, the processor is adapted to transmit and receive time-stamped activity, and/or compliance, and/or usage data with an external device.

In one embodiment, at least one sensor is a pressure transducer adapted to detect status of a dressing, and wherein the processor is adapted to use an input from the pressure transducer as a conditional input for an algorithm.

In one embodiment, the processor is adapted to determine a time threshold for a posture as a function of a patient's height. In one embodiment, the processor is adapted to analyze patient adherence to a prescribed activity level, including lower leg elevation and/or NMES device usage. In one embodiment, the sensor comprises one or more selected from accelerometers, ultrasound range detectors, piezoelectric sensors, gyroscopes, flex sensors, magnetometers, foot switches, smart textiles incorporating electrical sensing elements. In a further embodiment, the sensor comprises one or more selected from a hip-worn sensor to detect step counts and postural transitions, a thigh-worn sensor to detect walking, lying, sitting and/or standing events, and a sensor arranged to be worn on the lower leg to measure step counts, distinguish between standing, sitting, and lying and to measure lower leg elevation.

In one embodiment, the processor is adapted to operate according to the finite state machine paradigm. In one embodiment, the processor is adapted to define a user static state and a user active state. Preferably, the processor is adapted to define a state for a transition phase of pressure increasing and a state for a transition phase of pressure decreasing. In one embodiment, the processor is adapted to define a state for checking for user activity.

Preferably, the processor is adapted to execute a state machine algorithm in which:
    if the state machine is in the static state and an activity interrupt indicating a stepping motion is detected the processor moves the static state to an activity check state,
    if the state machine is in the static state and no activity interrupt or no-change in vertical height (Hv) is detected, the static state remains and the processor updates the time associated with the current posture,
    if the state machine is in the static state and there is no activity interrupt but a decrease in vertical height (Hv) is detected, the processor moves from the static state moves to a pressure-decreasing state, and
    if the state machine is in the static state and there is no activity interrupt but an increase in vertical height (Hv) is detected, the processor moves from the STATIC state to a pressure-increasing state.

In another aspect, the invention provides a computer readable medium comprising software code adapted to be executed by a digital processor to perform the steps of a processor of a system as defined above in any embodiment, including the steps of:
    receiving sensor data and processing said sensor data to determine user posture data including data indicative of vertical distance between level of the user's heart and ankle ($\Delta h$, Vd1, Vd2, Vd3), and
    based on said posture data together with a value for degree of user chronic venous insufficiency and/or blood density, generating an estimate of user static venous pressure while the user is static, without calf muscle pump activity.

DETAILED DESCRIPTION OF THE INVENTION

Brief Description of the Drawings

The invention will be more clearly understood from the following description of some embodiments thereof, given by way of example only with reference to the accompanying drawings in which:—

FIG. 11 shows a neuromuscular electrical stimulation (NMES) device of a system of another embodiment;

FIG. 12 is a functional block diagram of the stimulator unit of FIG. 11;

DESCRIPTION OF THE EMBODIMENTS

Figure 1:
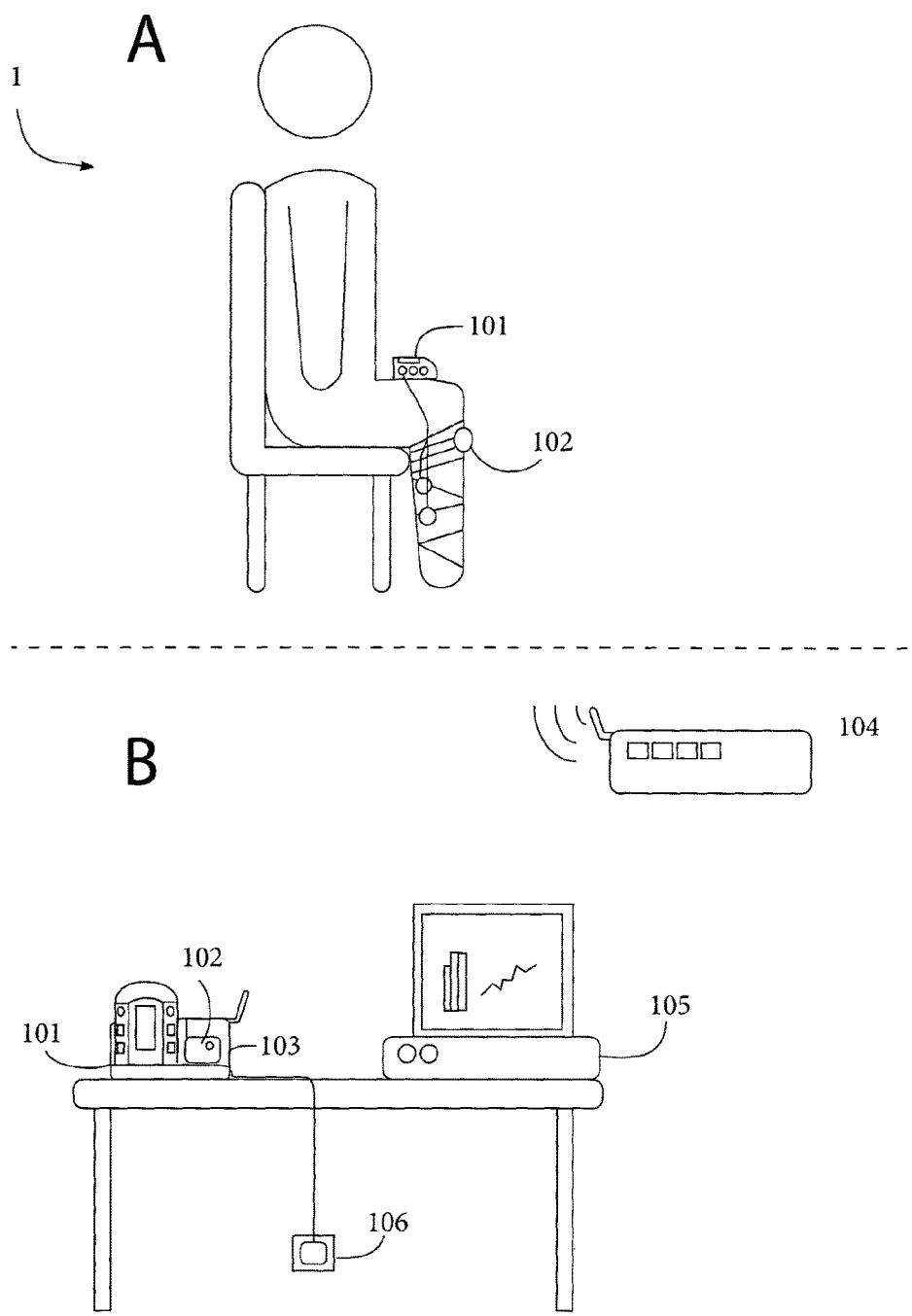
FIG. 1 is a general overview of the main components of a system of the invention in use.

FIG. 1 is a schematic view of a system 1 of the invention of one embodiment, in use. The system 1 comprises a battery-powered NMES device 101, and a wearable battery-powered sensor unit 102 for detecting data in order to determine venous pressure changes. A docking station 103 recharges the NMES and sensor devices, through a power outlet 106 when they are not being used by the patient. The docking station also facilitates transmission of time-stamped activity and compliance/usage data to a remote server 104 and to a PC 105 where it is stored for later access by patients and/or their carers or clinicians and can be viewed as softcopy or hardcopy reports.

A processor in the sensor unit 102 records and displays sensing and NMES data, and this data can be used to assess patient adherence to a prescribed program for alleviating venous pooling.

The processor implements algorithms which analyze sensor data to estimate venous pressure both when the patient is static and active. It alerts the user according to estimated venous pressure arising from posture status such as when prolonged periods of immobility or inactivity are detected. Also, the system may be integrated with existing compression therapies for ease of use in CVI patients. In this specification the term "static" means that the patient is not contracting the calf muscles which act as a pump. The term "active" or "activity" means that such contraction is occurring, such as when walking or not moving but nevertheless performing exercises to contract the calf muscles for venous pumping.

The system assists with the important aspects for alleviating venous pooling for the prevention and treatment of CVI, namely promotion of various postures and activities (such as walking, or exercises/interventions which activate the lower leg muscles) which help to reduce venous pressures, and the limiting of activities or postures which predispose and individual to sustained, elevated venous pressures.

The system of one embodiment on a continuous basis monitors posture and postural changes, monitors activity, and calculates venous pressure for both static and active phases. Also, it stimulates calf muscle contractions to promote venous blood flow and to compensate for reduced voluntary activity. It provides instantaneous patient feedback to warn of elevated venous pressure levels, and assesses patient adherence to prescribed patient activity levels, including for example lower leg elevation.

Under static conditions, the hydrostatic venous pressure, at a given point in a person's venous system, is directly related to the vertical distance between that point and the person's heart, the degree of chronic venous insufficiency, and blood density. Consequently the venous pressure can be calculated in various postures, under static conditions if the height of the individual and their trunk and leg lengths and orientations are known.

During activity (dynamic conditions such as walking or performing ankle exercises) venous pressure is determined partially by posture but also by degree of chronic venous insufficiency and/or several other parameters such as rate of muscle activity, body weight, height, calf circumference, and ankle range of motion. Consequently, venous pressure can be estimated under active as well as static conditions.

Monitoring of patient activity levels, i.e. time spent exercising, rate of exercise, step counts etc, is also important for helping clinicians to understand a patient's general health status. Tracking of this information by patients themselves may also aid patient compliance to treatment programs, and may facilitate goal-setting to encourage increased levels of activity.

A variety of sensor types (accelerometers, ultrasound range detectors, piezoelectric sensors, gyroscopes, flex sensors, magnetometers, foot switches, smart textiles incorporating electrical sensing elements) and positions (hip, thigh, lower leg, ankle, sole of the foot) can be used alone or in combination with each other to determine activity, posture and lower leg elevation. Different sensing configurations may be used to suit a variety of circumstances.

Figure 2:
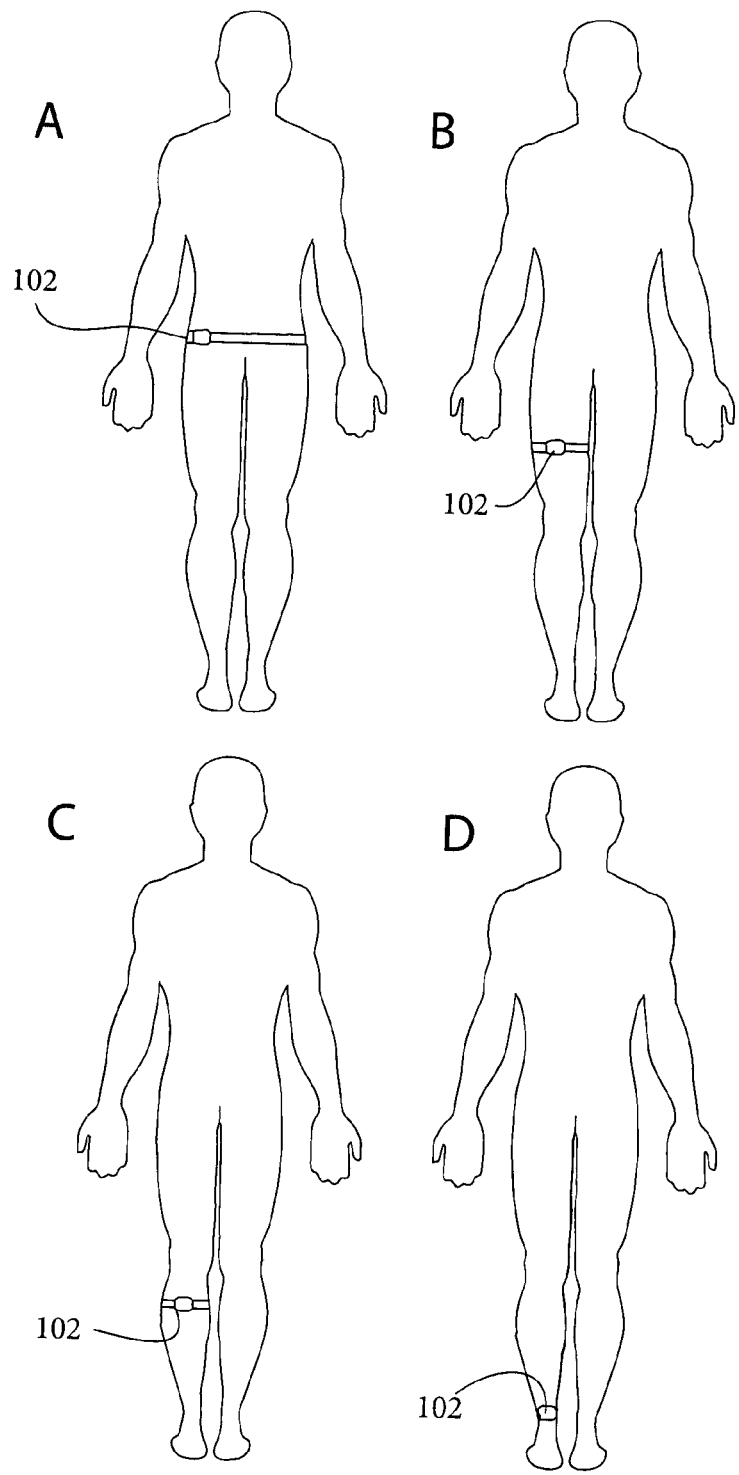
FIG. 2 shows possible locations for wearing sensors on the trunk and legs.

FIG. 2 shows a number of possible sensor positions that can be used to measure posture, activity and lower leg elevation using accelerometers and gyroscopes. By measuring the acceleration and tilt of a limb segment in one or more axes, posture and activity levels can be determined. FIG. 2 shows (A) a sensor 102 worn on the hip to detect step counts and postural transitions; (B) the sensor 102 worn on the thigh to detect walking, lying/sitting and standing events; and (C and D) the sensor 102 worn in two different positions on the lower leg, which arrangement can be used to measure step counts, to distinguish between standing/sitting and lying and to measure lower leg elevation.

Figure 3:
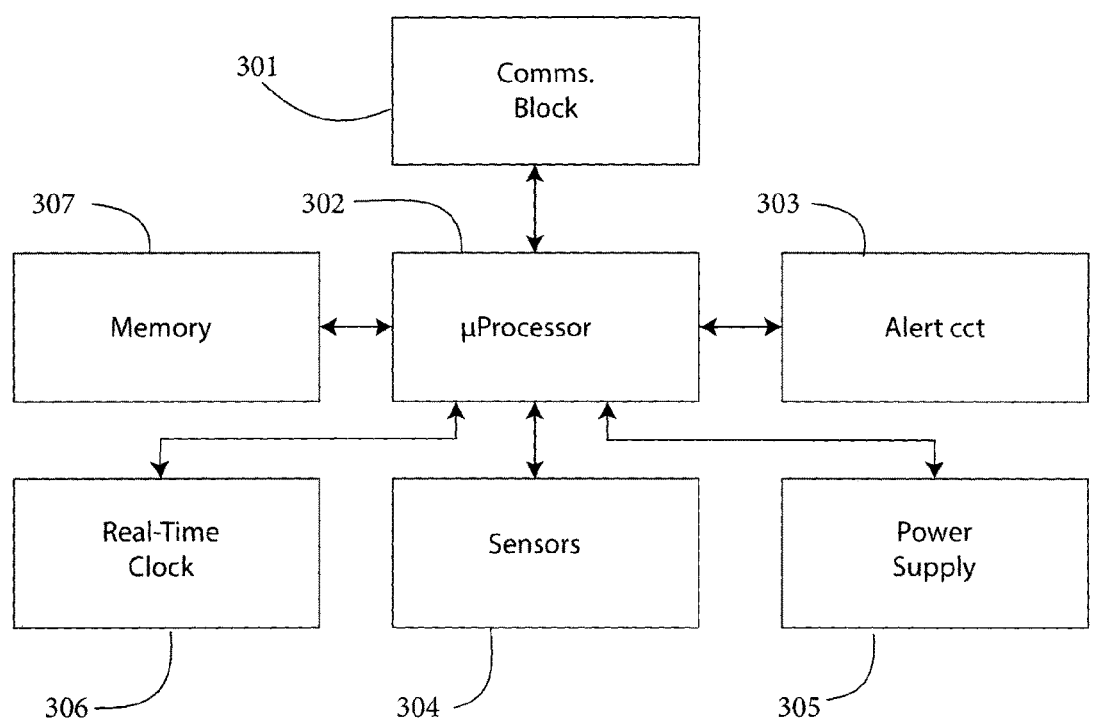
FIG. 3 is a functional block diagram of a sensor unit of the system.

FIG. 3 shows a block diagram for the system 1 circuitry. The system 1 comprises a communications block 301 to facilitate two-way wired or wireless communication to external devices; a microprocessor 302 for control of the system; alert circuitry 303 to provide the wearer with visual, tactile or audio feedback indicating a pre-determined postural or activity threshold has been exceeded; a variety of sensors for detection of postural data and activity levels 304, a power supply circuit 305 to facilitate powering and recharging of the device, a real-time clock circuit 306 to facilitate time stamping of activity and posture data, and a memory block 307 to facilitate storage and buffering of data.

Figure 4:
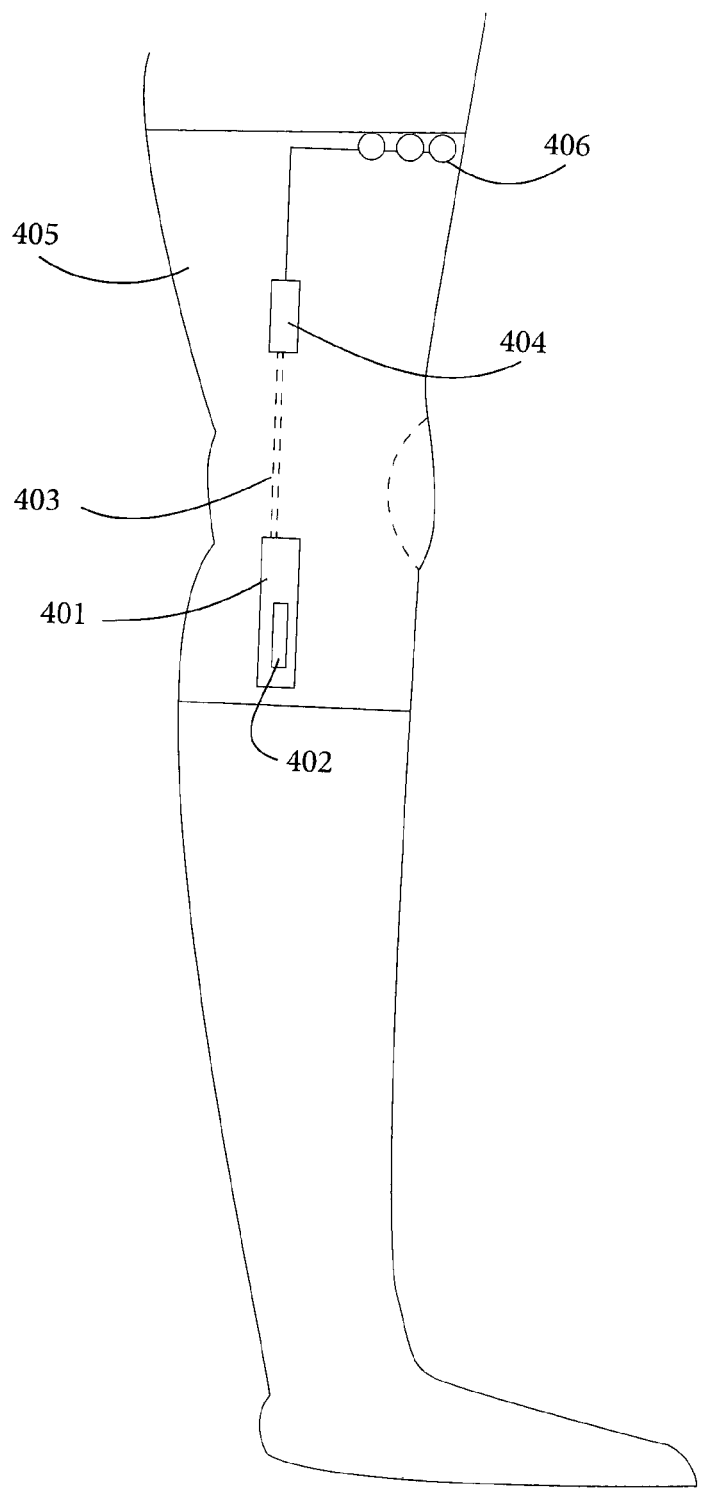
FIG. 4 shows sensors incorporated into a garment.

In a preferred embodiment the sensing block 304 comprises two tri-axial accelerometers for sensing of postural and activity levels by analysing the static and dynamic accelerometer signals in each measured axis (FIG. 4). Two accelerometer sensors (404, 402) are used to provide better identification of posture by comparing the orientation of the upper and lower leg. To achieve this one accelerometer 402 is placed distal to the knee joint, on the tibial ridge of the lower leg. The other one, 404, is placed proximal to the knee joint along the anterior midline of the upper leg. The accelerometers are incorporated into a garment 405 along with a control unit 401, for ease of donning and doffing and are connected via conductive wires routed under or through the garment 403. The garment may also incorporate status light emitting diodes 406 which are indicative of a high level of venous pooling (red), a moderate degree of venous pooling (orange) or a low level of venous pooling (green).

Figure 5:
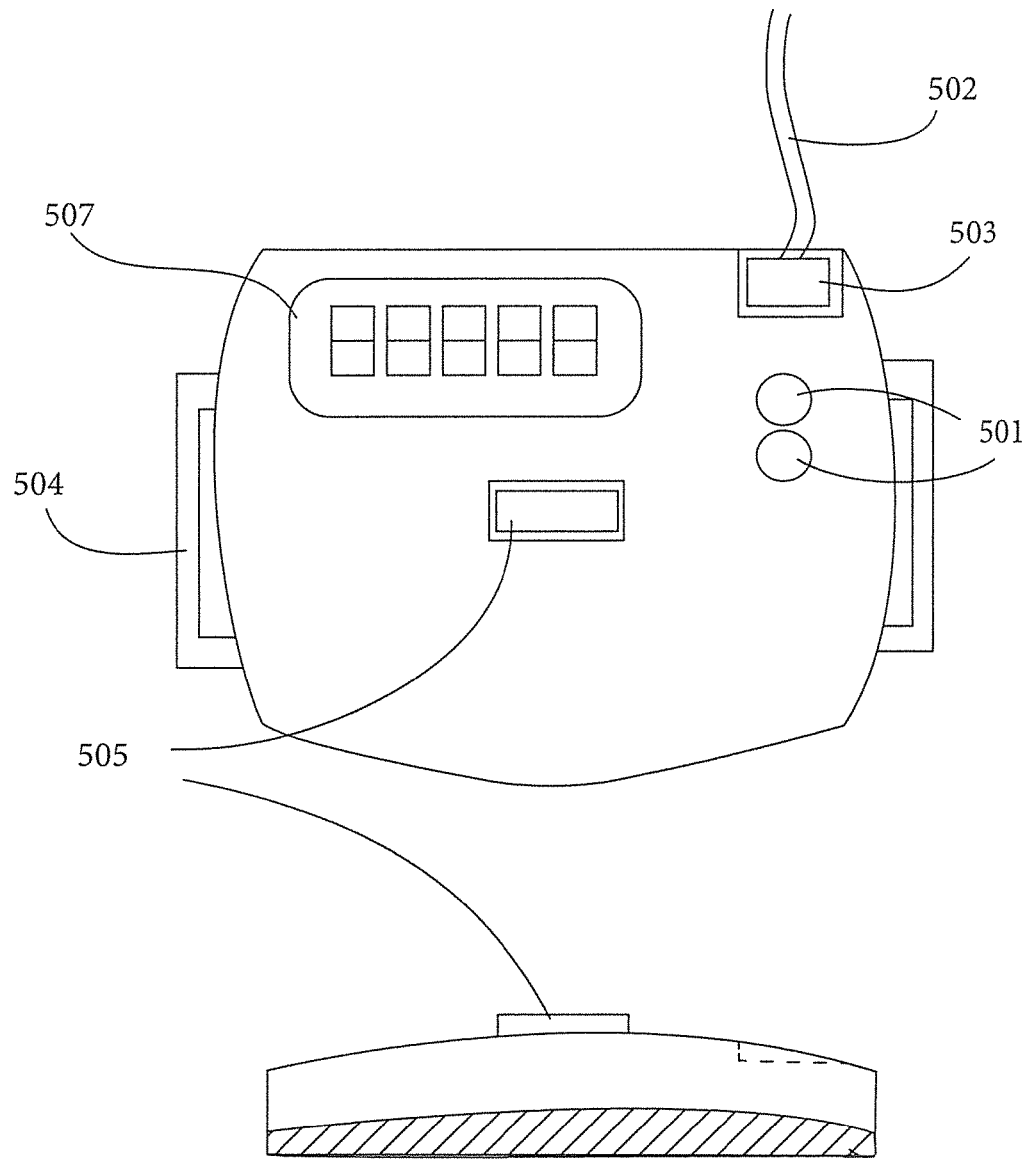
FIG. 5 shows one possible configuration for the enclosure of the sensor unit.

A more detailed illustration of the control unit 401 and distal sensor 402 is shown in FIG. 5. There are status light emitting diodes (LEDs) 501, to provide visual feedback to the user. The control unit 401 may also comprise a tactile actuator, such as a vibration motor which provides mild sensory stimulation as a more discreet form of feedback.

Belt hooks 504 facilitate mounting of the unit 401 on an elastic belt/strap which can then be attached to the lower leg. The presence of a belt (passing over the front of the device) may facilitate the inclusion of a compliance monitoring switch 505, which is pressed when the belt is firmly attached to the sensor and wrapped around the leg, indicating periods when the device is in use. The sensor may also comprise wired (502, 503) or wireless connections to external devices such as the NMES device 101 and docking station 103, additional sensor elements 404 or status LEDs 406. Finally the control unit 401 also incorporates an alphanumeric display 507 for displaying measured parameters and estimates of venous pressure time integral.

The system achieves monitoring of venous pressure during static and active conditions by analyzing the accelerometer signals which identify a postural change to a static posture or an activity which can be achieved using thresholds. When a new postural change is detected the sensor estimates the venous pressure profile for the posture or activity since the last postural change. The venous pressure profile estimation for a given interval will depend on whether a static posture was maintained or an activity was carried out in that interval.

In general terms the system processor processes sensor data to determine user posture data including data indicative of vertical distance between level of the user's heart and ankle, and based on this data generates an estimate of user static venous pressure while the user is static, without calf muscle pump activity. Preferably, it also determines from the sensors if there is calf muscle pump activity, and generates an estimate of user venous pressure according to the above static venous pressure estimate along with the rate of calf muscle activity and a value for degree of user chronic venous insufficiency. The value for degree of user chronic venous insufficiency is preferably a CEAP value, as this is a well-known standard scale. The rate of calf muscle activity is preferably determined by changes in acceleration detected by the accelerometer located on the lower leg. These rapid changes in acceleration are caused by impact forces created during impact of the user's heel during calf muscle activity.

In some applications the wearable sensor unit could act as a data logging unit, saving the raw sensed data to internal memory for post-processing at a later stage. In this post-processing step the raw data is uploaded to another device with a fast processor in order to apply all of the venous pressure estimation algorithms. This allows a smaller, less complex processor to be used in the wearable sensor and may also offer power saving benefits as the processor isn't required to carry out complex mathematical operations. However this approach would limit the types of alerts that could be provided to the wearer in real-time. It will be appreciated that the term "processor" is not limited to a single device, but could be multiple devices, possible at different locations. The links may be wired or wireless, remote or local.

Static Venous Pressure Estimation

Figure 6:
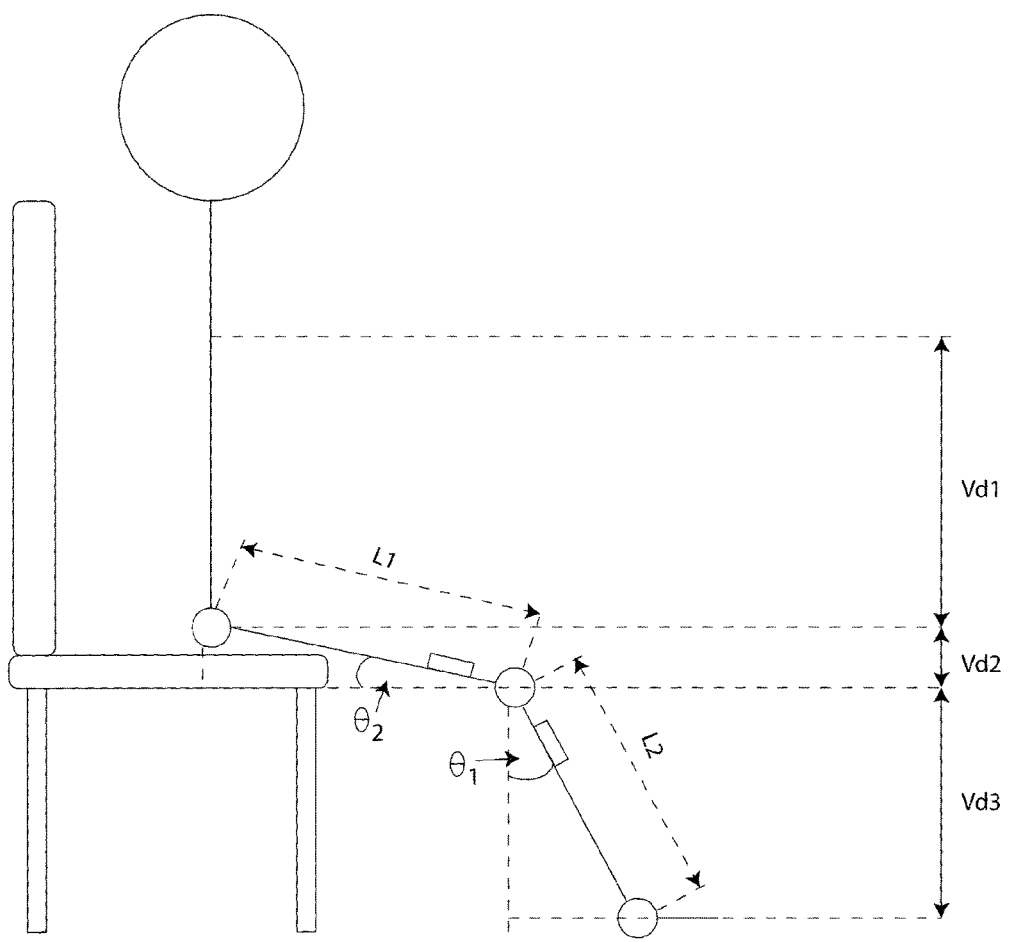
FIG. 6 is a diagram showing how static venous pressure is calculated using postural data joint angles determined from sensors.
Figure 7:
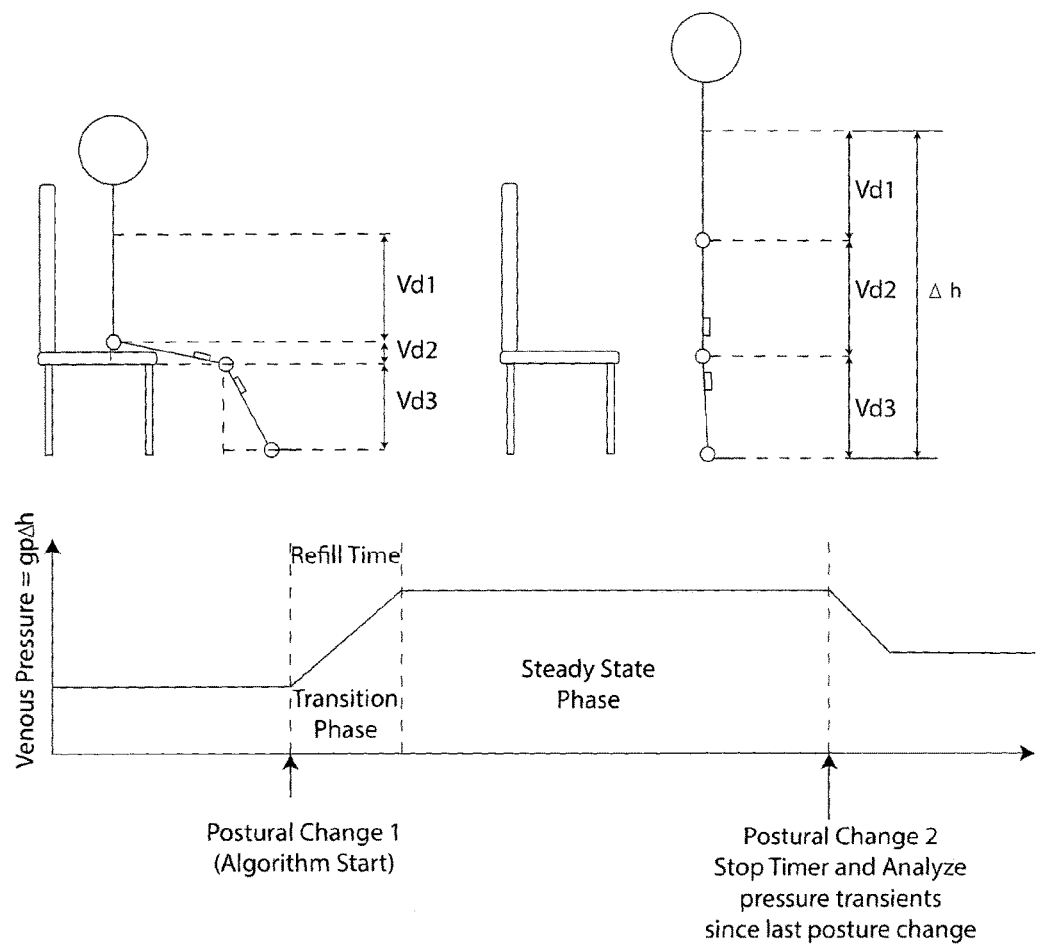
FIG. 7 shows two postures illustrating a postural transition from sitting to standing and the corresponding venous pressure waveform.
Figure 9:
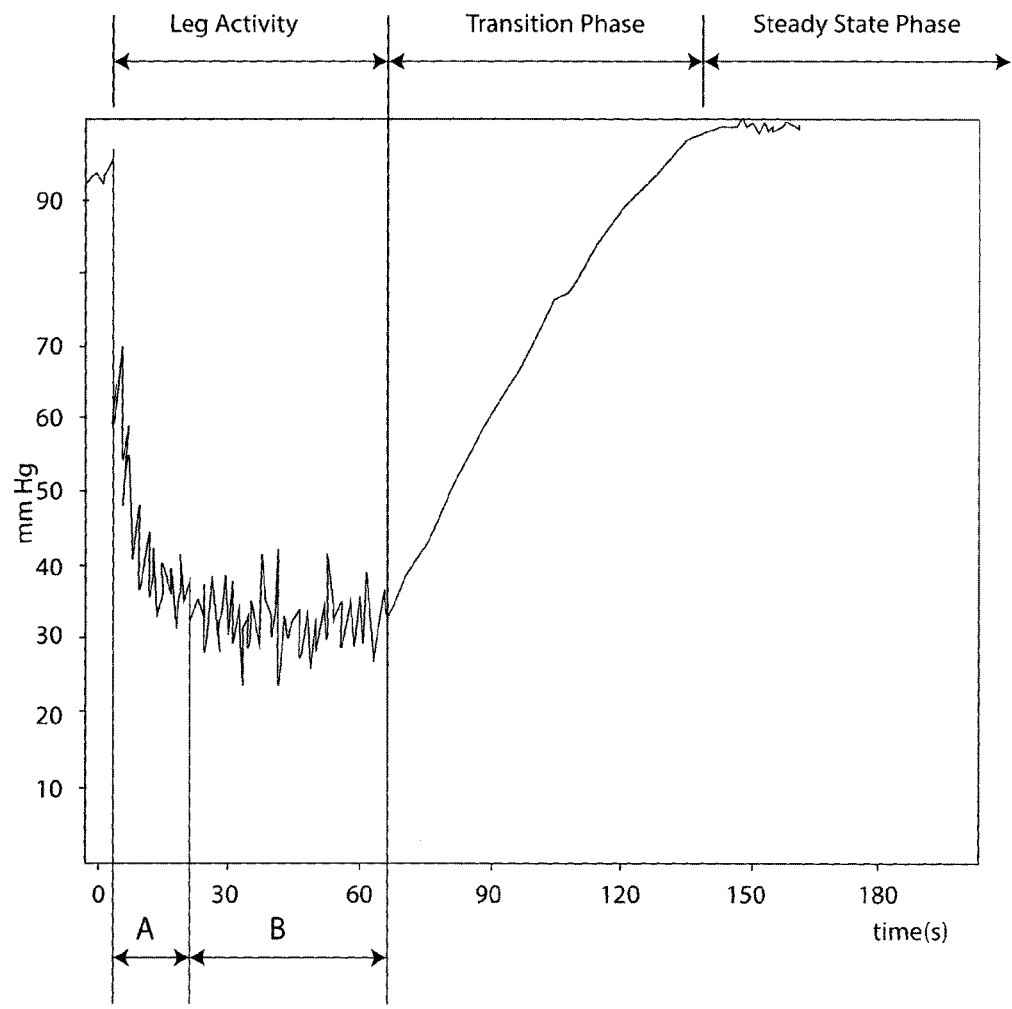
FIG. 9 shows a static and active venous pressure as a pressure waveform during walking, a transition phase, and a steady state phase.

During static conditions venous pressures stabilizes, as shown by the plot of FIG. 9. Venous pressure during the static phase can be estimated by measuring the orientation of the trunk, thigh and shank body segments (FIGS. 6 and 7). If the distance between the heart and hip (Vd1), thigh length (L1), and the distance between the knee and ankle (L2) are known, then the overall vertical distance from the heart to the ankle can be calculated using tilt angles from the accelerometers. Assuming a vertical trunk orientation (during sitting or standing) the tilt of the thigh and shank can be measured by examining the gravity component in relation to each of the accelerometer axes placed on both the shank and thigh and using an inverse trigonometric function to determine the total vertical distance between the ankle and the heart $\Delta h$, by adding Vd1, Vd2 & Vd3. Venous pressure can then be calculated by using the equation for hydrostatic pressure:

$$\text{Hydrostatic pressure} = \rho g \Delta h,$$

Where $\rho$ corresponds to the density of blood (~1052 kg/m$^2$), g corresponds to the acceleration due to gravity, and $\Delta h$ corresponds to the vertical distance between the ankle and the heart. In individuals with standard blood density the value of $\rho g$ is 0.77 mmHg/cm, i.e. venous pressure increases by 0.77 mmHg for every 1 cm increase in $\Delta h$.

The sensor can facilitate manual input of the length of the trunk, thigh and shank (distance from the ankle to the knee joint) for calibration of the system so that an accurate estimate of venous pressure may be determined.

Figure 8:
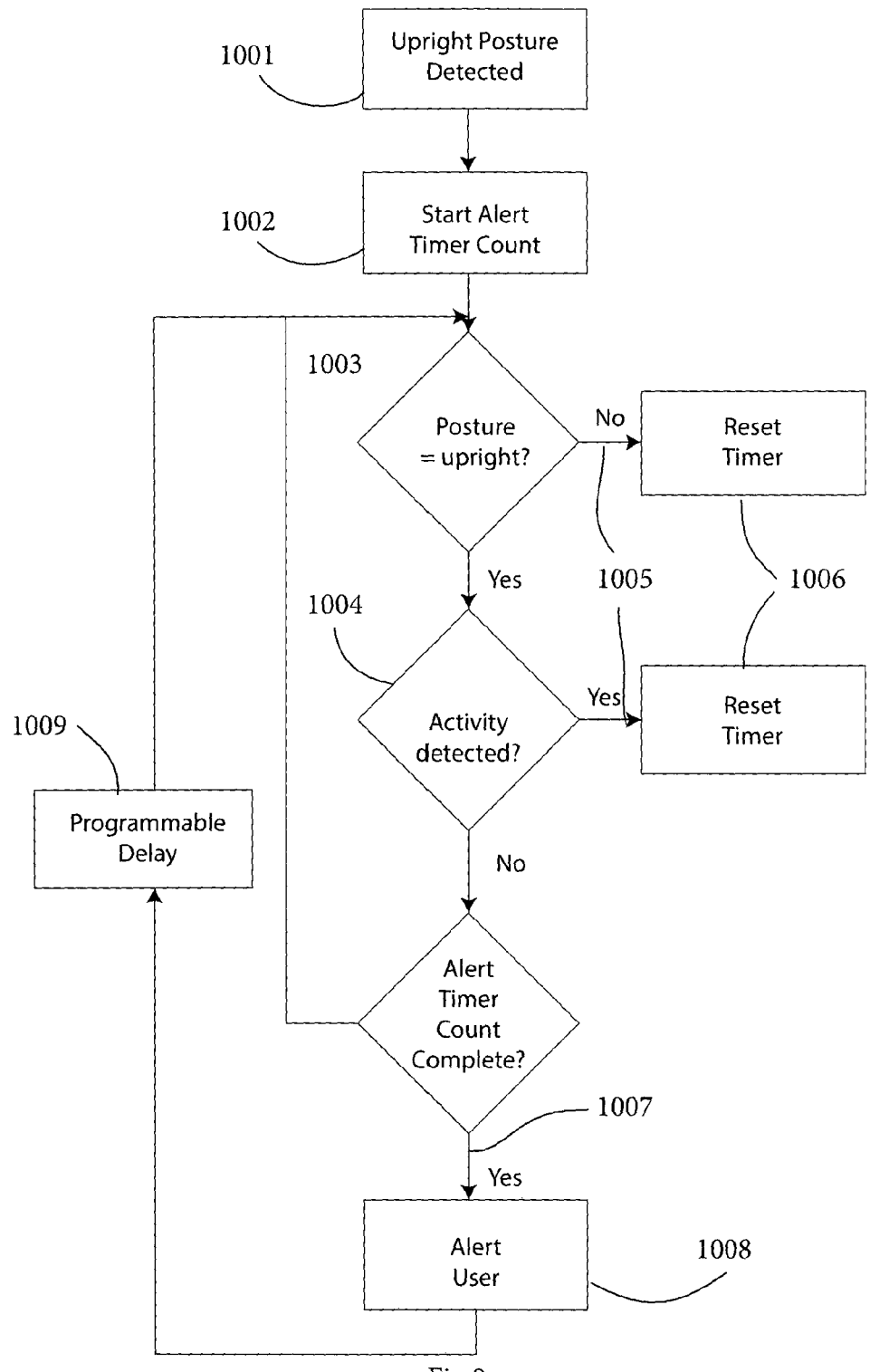
FIG. 8 is a flow diagram for the system controller to generate an alert based on a determination of venous pooling.

A sample algorithm for detecting and logging venous pressures is outlined in FIG. 8. When the algorithm begins (1001, 1002) a timer is started and the initial posture/activity is tracked (1003) from a previous postural transition. When a subsequent postural change is detected, this marks the end of the initial posture. The timer is then stopped (1006) and the pressure profile for the period of the previous posture/ activity is calculated (1007). The delay between loops is programmed (1009).

The calculation of the pressure profile for a static posture depends largely on $\Delta h$. For more accuracy in the estimation the refill rate of the veins, which is largely determined by the degree of chronic venous insufficiency (CVI) of the user should be included in the algorithm. This may be inputted as a configuration setting of the system. The dynamic (active) pressure measurements depend more heavily on the degree of CVI and rate of calf muscle pump activity.

Following a postural change consisting of a change from one static posture to another, the venous pressure waveform (FIG. 7), measured at the level of the ankle is biphasic, comprising: a transition phase lasting for the length where venous pressure increases or decreases linearly due to a change in $\Delta h$ and a steady state phase where the venous pressure is fixed. The length of the transition phase (refill time) is determined by the function of the venous valves and the degree of chronic venous insufficiency and the arterial inflow and will vary for each individual. The refill time can be inputted as a specific input, measured for this patient, or it can be selected from a pre-set value by the processor based on the patient's degree of chronic venous insufficiency. Refill time can be determined for an individual and programmed into the sensor using indirect measurement of their venous haemodynamics using air-plethysmography, or direct venous pressure measurements. Alternatively refill times may be estimated based on degree of chronic venous insufficiency (i.e. CEAP class or equivalent), which can be programmed by a clinician or the user into the sensor.

If the interval being analyzed is less than the refill time, then a postural change occurred during the transition phase. The pressure at the time of the current posture can be determined from the starting pressure value and the interval time multiplied by the refill rate (change in pressure during the transition phase divided by the refill time). The average of the previous and current pressures will give the average pressure during the transition phase. This average value and the interval value are then stored to memory.

If the interval time is greater than or equal to the refill time than the average pressures during the transition and during the steady state period need to be saved separately. The average pressure during the transition can be determined by averaging the pre-transition pressure and post-transition pressure which are determined directly from the ρgΔh value of the start and end static postures. This average pressure is then stored with the refill time. The steady state pressure is also stored along with its duration.

By storing the average pressures for a given phase along with their respective durations, a pressure time integral can be estimated which can give the users or clinicians a continuous projection of pressure changes during static postures and postural transitions (achieved by multiplying the average pressure by its associated time). This pressure-time integral is reported to the users and clinicians and thresholds may be set to trigger alerts in the form of visual, tactile or audible feedback if the pressure time integral exceeds a predefined value.

Active Venous Pressure Estimation

During movement, venous pressures are modulated by the activity of the lower leg muscles, which have a pumping effect on the veins of the lower leg, which helps to alleviate venous pooling. Consequently during voluntary or electrically stimulated contractions of the lower leg muscles, venous pressures are intermittently depressed immediately following muscular contractions and rise again in the post contraction period when venous refilling occurs. As a result, venous pressure during activity (venous pressure during voluntary or involuntary exercise) is determined in part by Δh, rate of muscle activation, calf circumference, degree of chronic venous insufficiency and ankle joint range of motion. The most important parameter is the degree of chronic venous insufficiency, and indeed this is sufficient together with the postural data to perform a satisfactory estimation of venous pressure during activity.

Figure 10:
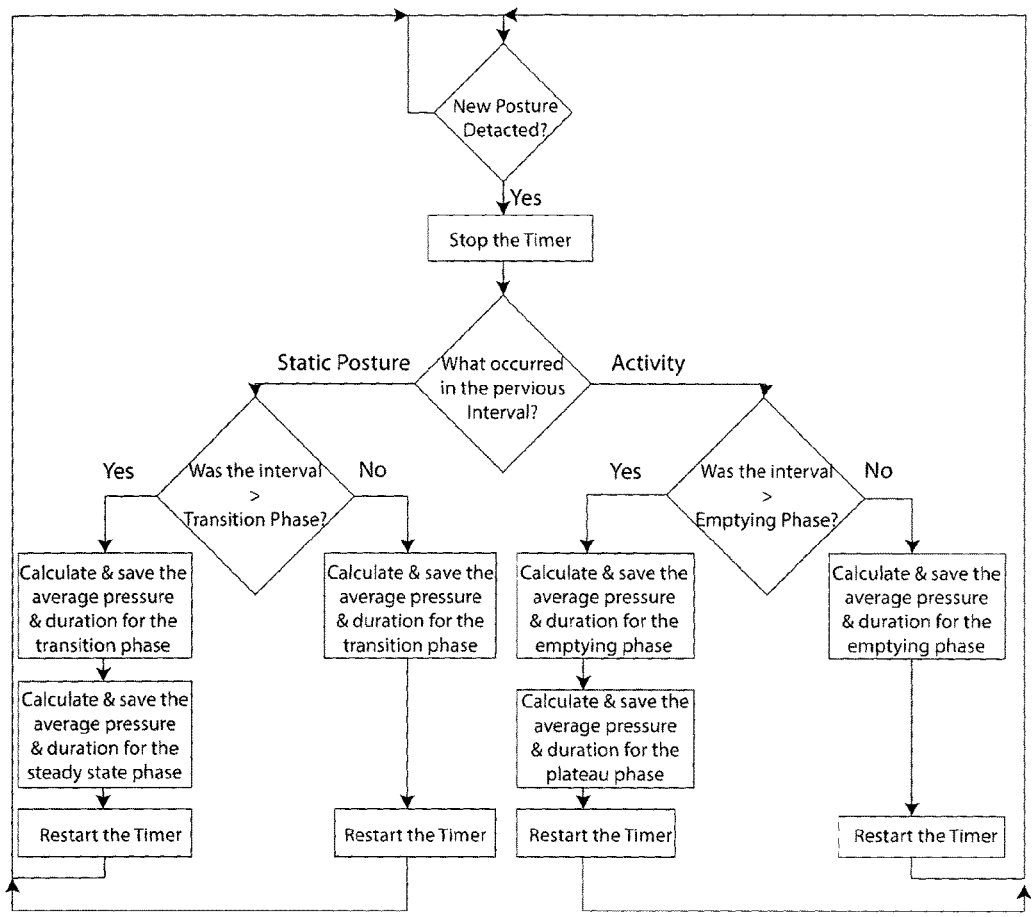
FIG. 10 is a flow diagram for operation of the system controller to analyzing and recording venous pressure profiles during static, transition, and activity phases.

FIG. 9 illustrates the changes well, and the positively-sloped ramp between active and static phases. The flow diagram of FIG. 10 shows how such phases are monitored and used to generate pressure profiles. The venous pressure profile during lower leg activity can be divided into two primary phases: an emptying phase (A) and a plateau phase (B) where the veins don't empty any further and venous pressure is maintained at a depressed level. The mean slope of the pressure change in the emptying phase is determined by the rate of muscle activation (i.e. stepping rate/walking speed), Δh and ankle range of motion. The minimal pressure in the plateau phase is determined by the degree of chronic venous insufficiency, calf circumference, ankle range of motion and Δh. If the slope of the emptying phase and the minimal pressure of the plateau phase are known, the mean pressure and duration of each phase can be saved to memory and will provide a good estimate of pressure time integral during that activity.

The slope of the emptying phase and the minimal pressure in the plateau phase for an individual can be obtained from direct venous pressure measurements or air plethysmography assessments and programming it directly into the stimulator. Alternatively the slope may be estimated by measuring the rate and strength of muscle activation or stepping and comparing by analyzing the dynamic accelerometer signals, calculating Δh, (which can also be determined from the accelerometer waveforms) and calculating a slope based on existing standardized values from direct venous pressure measurements. Ankle range of motion can also be programmed into the sensor to adjust the calculated slope. A poor ankle range of motion (e.g. a ankle range of motion <40°) would scale the slope by at least a factor of 2, making emptying twice as slow. A normal ankle range of motion would have no scaling effect on the slope of the venous emptying phases.

Similarly, the minimal pressure in the plateau phase can be determined by the degree of chronic venous insufficiency, the calf circumference, the ankle range of motion (programmed into the stimulator) and Δh which is determined from the static accelerometer signals. These parameters can be used to look up standardized values for the minimal pressure levels, permanently stored in the memory of the stimulator unit.

Venous Pooling Alert Algorithm

The system preferably has sufficient memory to accommodate logging of the raw sensor data. Post processing can be carried out on the data to determine the parameters of interest (time stamped activity data, posture data, leg elevation and daily venous pressure estimates) for report generation. Ideally, the sensor would incorporate one or more algorithms to facilitate real-time detection and estimation of venous pressures based on sensed postural and activity data.

As referred to above FIG. 8 illustrates an example program flow for such an algorithm. When an upright posture is detected (1001) a timer is started 1002. The timer counts to a predefined time value, which represents the allowed time for the user to maintain a static upright posture. As the timer counts, the posture (1003) and activity (1004) of the user is periodically checked, if the user changes from an upright posture or commences activity (1005) the timer is reset (1006). If the user exceeds the allowed duration for static upright posture (1007), the sensor devices alert the user (1008) to the risk of venous pooling via audio, visual or tactile feedback. Once the user has been alerted the alarm system is halted using a programmable delay (1009), before posture and activity checking begins again. If a posture change or activity is detected, the timer is reset and the process halts until an upright posture is detected again. If a posture change or activity is not detected, the sensor system will alert the user again once a programmable delay has expired. The alerted system may be programmed to avoid the device becoming an irritation to the user, either through the use of a very long alert hold-off delay or through the use of a user-controlled interrupt, which might halt the algorithm for a predefined period.

NMES Devices

The invention in some embodiments uses the venous pressure estimation outputs to achieve improved artificial blood flow through neuromuscular electrical stimulation (NMES) of the foot and leg of the affected side for the prevention, treatment and management of various manifestations of CVI. NMES improves venous return from the legs of CVI patients, when used in conjunction with compression bandaging, leading to an improvement in the healing rates of venous leg ulcers.

NMES can be delivered in two ways, through the use of surface electrodes ("surface NMES") or through implanted techniques called "implanted NMES". We would envisage NMES to be delivered predominantly through the use of surface NMES as it is less invasive. However in circumstances where surface NMES is impractical, i.e. for the long-term prevention of venous leg ulcers, implanted NMES may offer a more convenient solution.

There may be ambient activation of devices such as implanted micro-stimulators, such as the BION system (G. Loeb, F. Richmond, J. Singh, R. Peck, W. Tan, Q. Zou, and N. Sachs, "RF-powered BIONs™ for stimulation and sensing," in *Engineering in Medicine and Biology Society*, 2004. *IEMBS'04. 26th Annual International Conference of the*

*IEEE,* 2004, pp. 4182-4185). This approach makes implanted NMES devices more suitable for long term applications involves embedding the control and RF circuitry into a household object for convenient activation of NMES using the implanted device.

Surface NMES

An NMES device is shown in FIG. 11. It is for connection to the lower extremity of the patient via wires which connect to one or more stimulus output port 1109 on the device and surface electrodes placed on the intended stimulation site. It has a simple user interface 1101 to display status messages and alerts and has controls to allow the user to control and test the amount of stimulation they would like to select (1102-1107). The NMES device is portable and discreet enough to be worn on the hip or in a pocket. In addition to providing an electrical connection to the electrodes, a wired connection can also be used to provide a data and power connection to a sensor unit and/or docking station via additional sockets 1110 on the stimulator. Furthermore, the device should be able to accommodate a range of external additional sensor inputs 1108 for the development of more sophisticated stimulation algorithms. In a preferred embodiment, this sensor input may comprise levels of venous pooling, leg elevation or activity levels.

The NMES device is programmable so that typical stimulation parameters such as: stimulation amplitude, pulse width, frequency, stimulation envelope: ramp-up, ramp-down, on and off times, number of channels and the stimulation schedule may be programmed. This can be done directly by the clinician or may be selected automatically on the basis of a range of sensor inputs such as levels of venous pooling, leg elevation and activity levels. For example, if an individual is found to have excessive levels of venous pooling in a given day, an increased duration of stimulation or additional stimulation sessions are recommended to counteract the excessive pooling observed. Additionally, stimulation parameters such as duty cycle, stimulation frequency or intensity may be adjusted to provide a more intensive stimulation session which provides greater hemodynamic benefit. Thus, the system is capable of an adaptive response to the degree of venous pooling in such a way that it ensures maximum venous return and user comfort. The stimulator unit should also be capable of acting as a portable programming interface to the sensor unit.

A general block diagram of the NMES device of FIG. 11 is shown in FIG. 12. The device comprises: a microprocessor block 1201 for overall control; stimulus generation circuitry on one or several channels 1202; flash memory 1203 for storing programs, sensor and usage data; a real-time clock 1204 to facilitate patient compliance monitoring and algorithm detection; a communication block 1205 to facilitate two-way wired or wireless communication to external devices; a sensor interface 1206 to accommodate a range of external and internal sensors; and power supply circuitry 1207 for regulation of the power supply to the device and to facilitate recharging.

In one embodiment any of the following elements may be implemented on a mobile phone running an NMES application: overall control of the system 1201, memory storage 1203, real time clock 1204, the communication block 1205, the sensor interface 1206 and the power supply circuitry 1207. The stimulus generation circuitry 1202 is implemented on an external device attached to the mobile phone via a wired or wireless connection.

Figure 13:
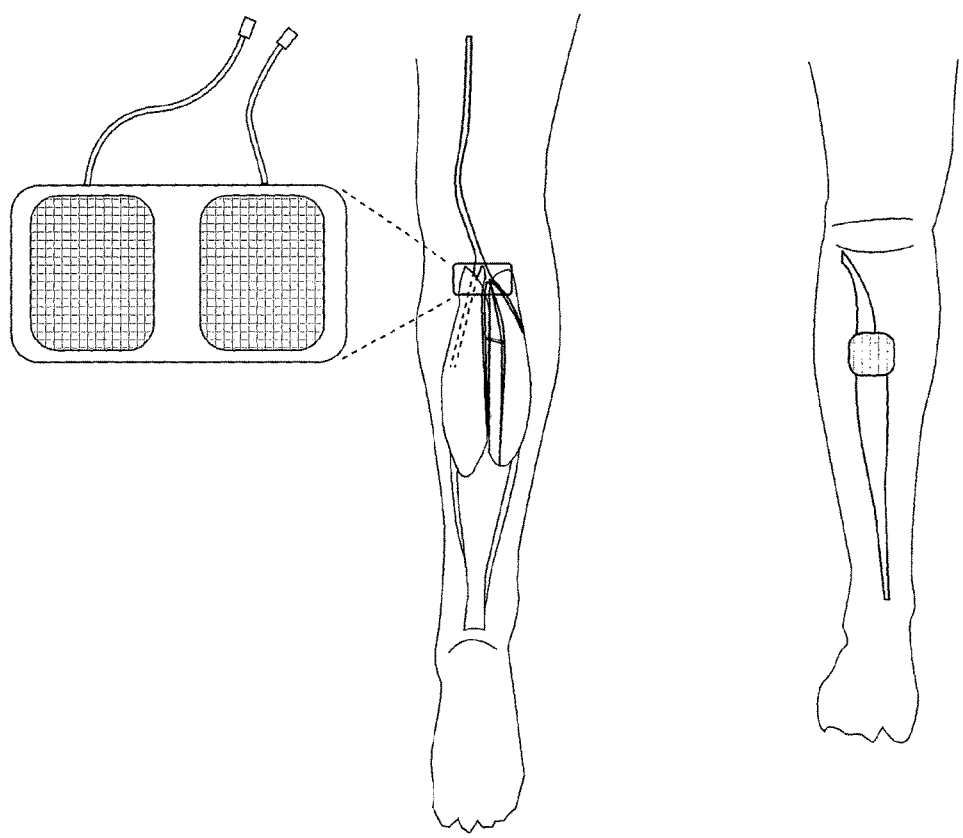
FIG. 13 shows an electrode design and placement which would facilitate stimulation of the anterior and posterior muscle groups of the lower leg.

In a preferred embodiment NMES is applied via surface electrodes to the tibial and peroneal nerves on the back of the knee. FIG. 13 illustrates an electrode design that allows for selective stimulation of the tibial nerve or the common peroneal nerve, which branches from the tibial nerve. Selectively stimulating the tibial nerve activates the muscles of the posterior compartment of the leg such as the soleus and gastrocnemius muscles. Selectively stimulating the common peroneal nerve selectively stimulates the muscles of the anterior and lateral compartments of the leg such as the tibialis anterior muscle. The electrode consists of two electrically conductive portions separated by a non-conductive portion, and must be placed substantially medial to the tendon of the biceps femoris. A reference electrode is required to complete the circuit and is placed substantially central to the bulk of the tibialis anterior. The advantage of such a configuration is that by alternating between stimulating the anterior and posterior/lateral muscle compartments, muscle fatigue will essentially be halved, allowing for extended periods of NMES therapy. This electrode configuration facilitates stimulation of the posterior muscles which would otherwise not be possible in leg ulcer patients, due to ulcerated skin restricting the electrode placement.

Control circuitry in the stimulator unit is provided to effectively use this electrode arrangement. The control circuitry is located on the output stage of the stimulus-generating circuitry of the stimulator device. The high voltage stimulus waveform required to generate a tetanic muscle contraction is generated by the stimulator output circuitry. The control circuitry selects which of the two conductive portions of the electrode will be connected to the stimulus output for the current stimulation cycle. One skilled in the art will recognise that a three-way H-bridge configuration is an effective way of implementing this control circuit.

Figure 14:
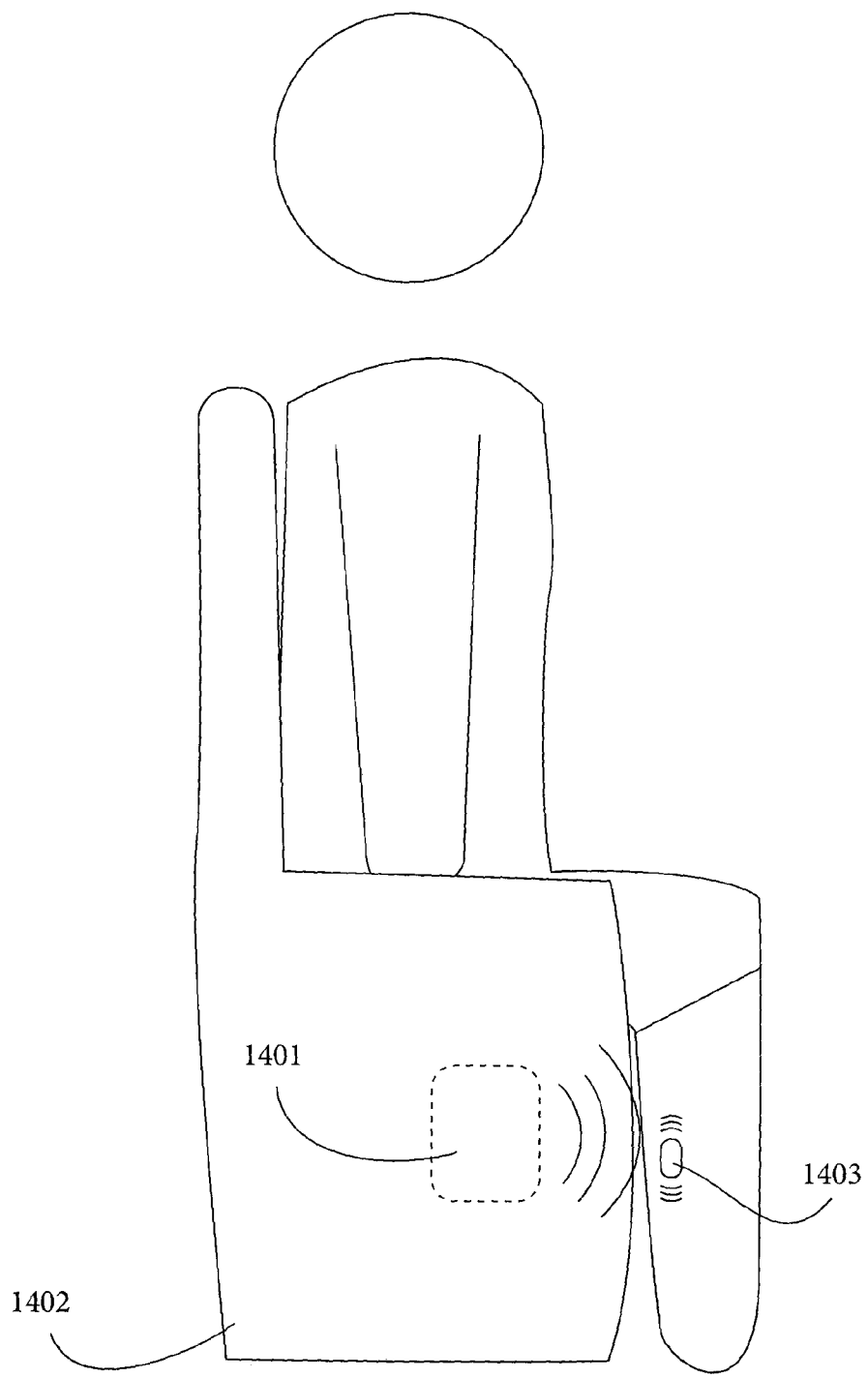
FIG. 14 shows ambient activation of an implanted stimulator.

Implanted NMES Techniques Using Ambient Activation:

FIG. 14 shows a preferred embodiment of the system for ambient activation of implanted NMES devices. RF transmission coils and control circuitry 1401 are embedded into an armchair 1402. When a user who has been implanted with an NMES device 1403 comes within a predefined range of the armchair, the control circuitry commences communication with the implanted device. NMES may commence immediately or following confirmation from the user.

Logging Data

In one embodiment, usage data from the NMES device and sensors is downloaded by plugging them into a docking station. The station could facilitate recharging of the system's batteries at night when the system is not in use as well as facilitate downloading/transmission of usage and sensor data to a PC, a remote server or to a desktop stimulator device which may have a colour display. This data could either be printed directly from the PC via a proprietary software interface or soft and hardcopy reports could be generated remotely and sent to the user, their nurse or other relevant stakeholders.

A summary of usage data would include:
 The date and time during the day when stimulation was applied.
 Intensity of stimulus.
 Duration of stimulation sessions.
 Device error messages.
 Duration and time of user activity, posture and lower leg elevation levels.
 Pressure Time Integral summaries & statistics.
 Additional summaries and statistics on individual or combined usage/sensed data.

This information is stored on a secure database, which can be accessed by the patient's physician. The offline data can be analysed to assess the effectiveness of the system, user compliance, and monitor patterns of patient activity. This information could be analysed for research purposes, or could be used by the clinician to assess the effect of the system on the user's quality of life, i.e. if the system is effective, the user may become more active, as indicated by increased periods of standing and activity, and greater numbers of sit-to-stand transitions etc. This reporting interface provides both reports and alerts on the patient's condition and may be customised for a number of management applications such as venous leg ulcer healing, venous leg ulcer recurrence prevention and varicose vein prevention.

A fall detection algorithm could also be incorporated into the control unit, using kinematic sensor data as input. Detection of a fall would trigger an alert (e.g. via GSM alert), to be sent to the clinician and/or primary carer(s).

Application of the System to Venous Leg Ulcer Healing

Figure 15:
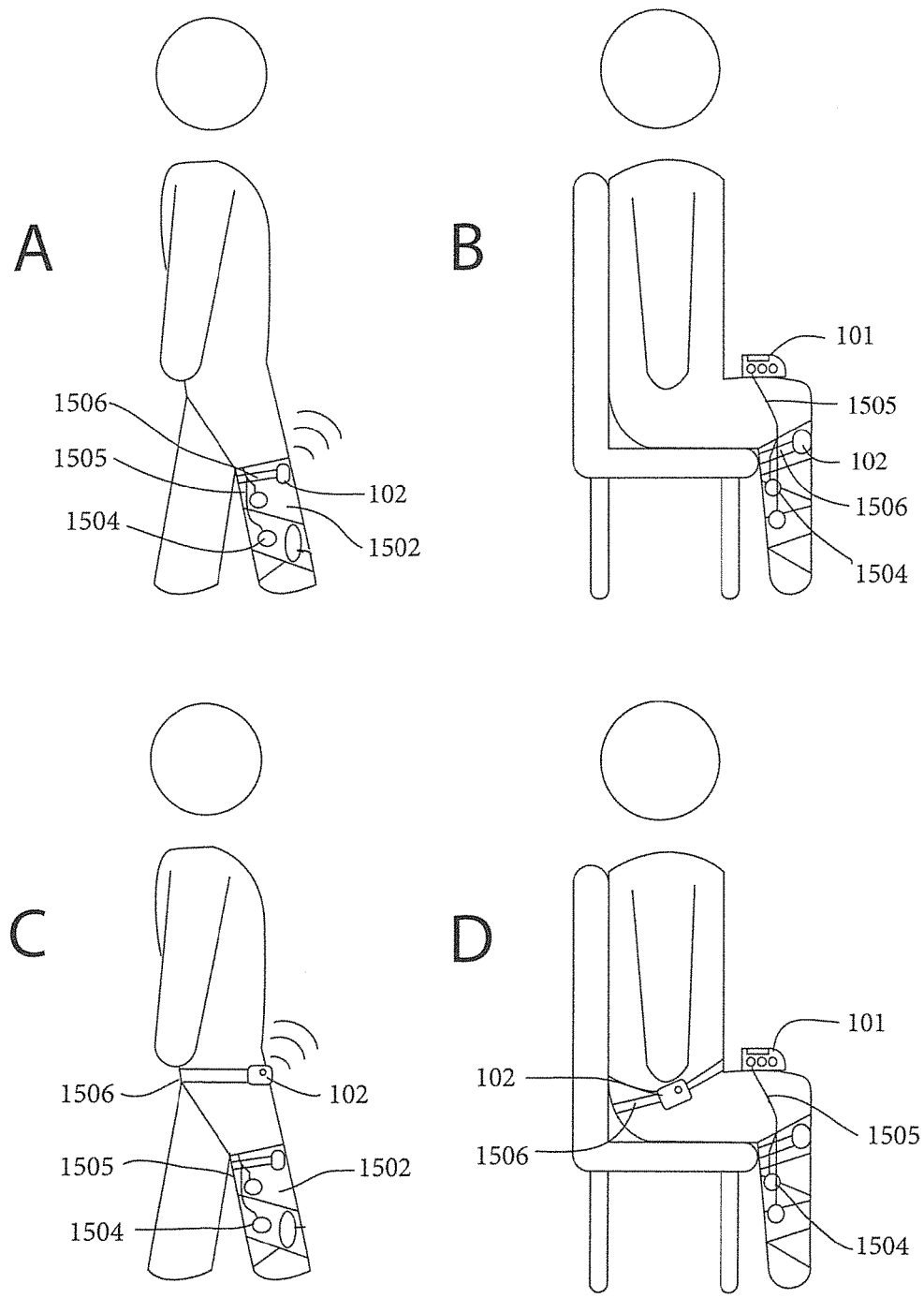
FIG. 15 is a set of diagrams showing a sample application of the system for venous leg ulcer healing.

One application of the system is for the treatment of active venous leg ulcers. A preferred embodiment of the system for this application is shown in FIG. 15. FIGS. 15A and C show an example use of the system, while the user is going about his/her daily activity. FIGS. 15B & D show the user carrying out his/her home-based NMES therapy. Two possible sensor positions are shown. In diagram A the patient is wearing compression bandaging 1502 as a standard part of their treatment. As shown in diagrams A and B the sensor device 102 may be worn on the lower leg. It may be fixed in place by placing it beneath the top layer of compression bandaging or with the aid of an elastic strap 1506. In this way users do not need to consider placing the sensor each day. Diagrams C and D show that the sensor device 102 may be worn on the waist with the aid of an elastic strap. The sensor device would be placed at the start of each day by the user, and taken off to be recharged at night. In the case of both the leg-worn and waist-worn sensor configurations recharging may be achieved through direct, wired connection to the NMES device or through the use of a docking station 103 which provides a connection to recharging circuitry.

Electrodes 1504 are worn to facilitate NMES stimulation of the lower leg muscles in response to the sensing of venous pressure, for the purpose of promoting venous blood flow. At least one of the electrodes is fitted beneath the compression bandaging on the lower leg. They are positioned to facilitate stimulation of those muscles which promote venous blood flow from the lower leg when contracted, preferably the soleus, tibialis posterior and tibialis anterior muscles. This may be achieved through nerve stimulation or through direct stimulation of the muscle belly.

FIG. 15, diagram B shows the system arrangement as the user carries out a prescribed NMES stimulation session. The NMES device 101 is connected to the electrodes 1504 via lead wires 1505. The user can set the NMES device to carry out muscle stimulation at an intensity level of their choice. At night, when the system is not in use, the devices can be placed in the docking station 103 of FIG. 1.

Application of the System to CVI Prevention

Figure 16:
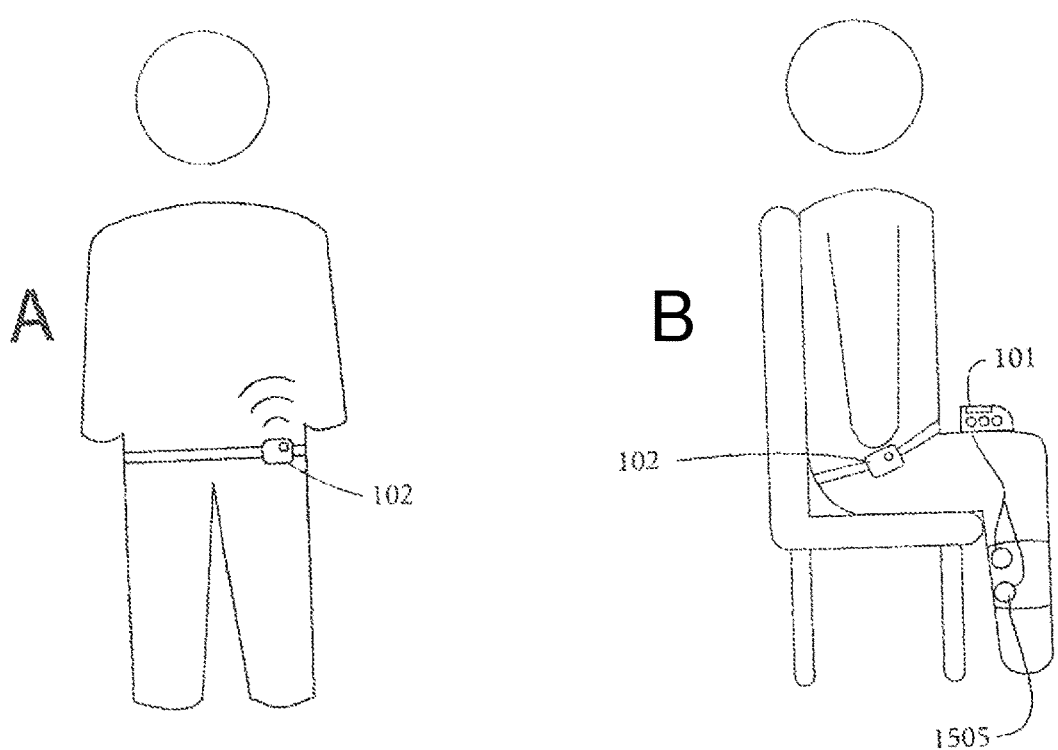
FIG. 16 shows a sample application of the system for CVI prevention.

A further application of the system is for the prevention of symptoms of chronic venous insufficiency such as varicose veins and venous leg ulcers. An alternative embodiment of the system for this application is shown in FIG. 16. FIG. 16, diagram A shows the system as it may be used during the daily activities of someone at risk of varicose veins or venous ulcers (i.e. people in a profession requiring prolonged periods of standing, or people with a history of venous disease). During daily activities the sensor device 102 alerts the user to prolonged periods of standing. The sensor device may be worn on the hip for convenience, using a belt clip or elastic strap.

With reference to diagram B of FIG. 16, the user may also use the NMES device 101 at home to promote their venous blood flow. The sensor and electrode positioning and/or routing of the NMES lead wires 1505 may be facilitated by the use of a garment such as a cuff which may incorporate activity and posture sensors and facilitates donning and doffing and correct electrode placement. At night, when the system is not in use, the devices can be placed in the docking station 103 of FIG. 1.

Garments for Electrode and Sensor Placement and Routing

It is envisaged that sensor and electrode positioning and/or routing of the NMES lead wires may be facilitated by the use of a garment 405 (FIG. 4). Each of these garments would facilitate:

- Electrode positioning, which may be achieved through the use of traditional gel electrodes which can be easily placed and routed through the garment or integrated electrodes which are woven into the garment itself.
- Placement of traditional discrete sensors which can monitor activity levels and lower leg elevation or integration of flexible sensors which may be developed using printed electronic technologies
- Low-profile routing of data and power connections through the garments using conductive threads or flat wire connections.

Pressure Estimation Using a State Machine

Figure 17:
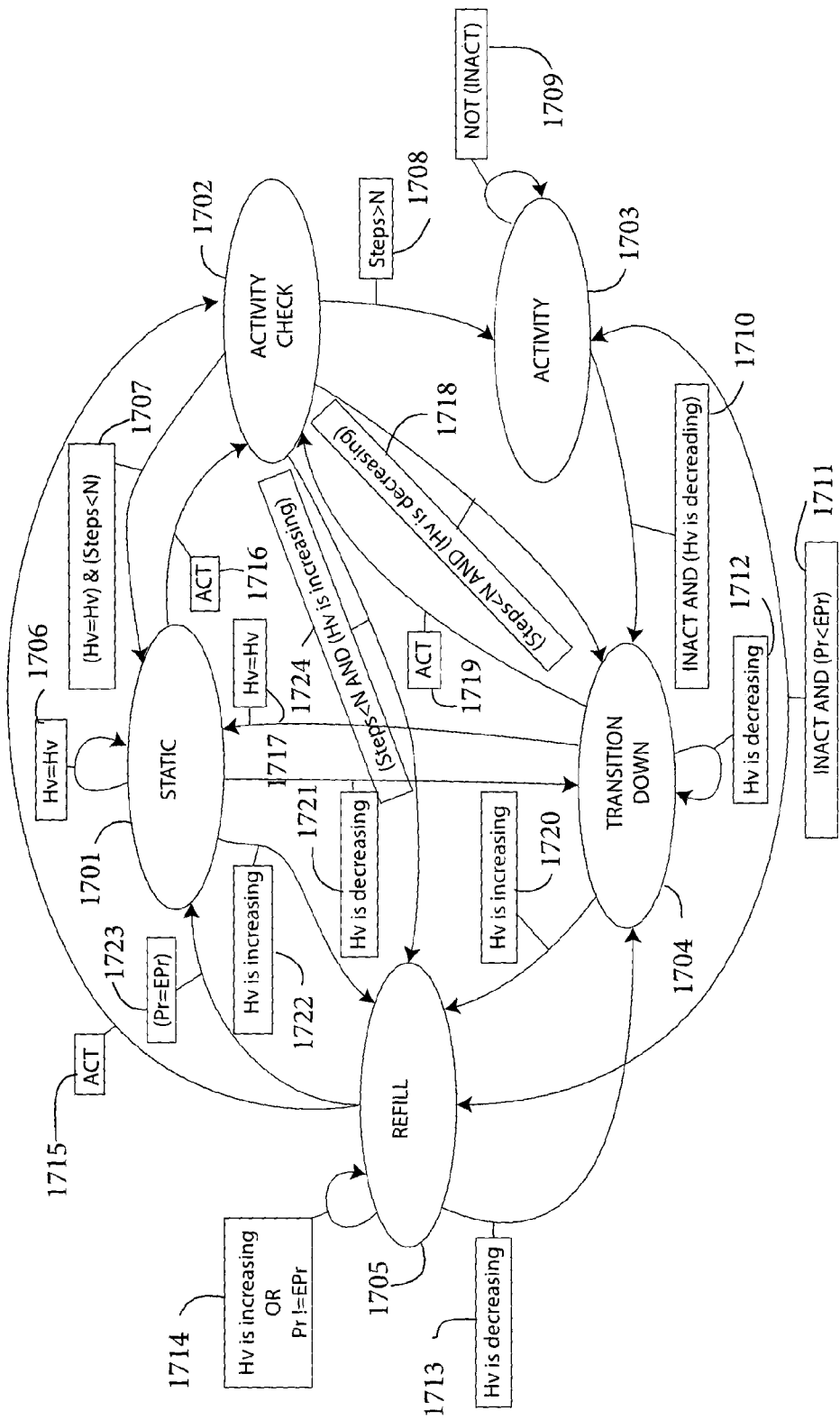
FIG. 17 is a state diagram for operation of the controller of a system of the invention.

Referring to FIG. 17 a controller of one embodiment includes a processor with a non-invasive venous pressure data logger structured around a state-machine design. Those skilled in the art will recognize that the state machine structure provides a program flow structure for logging of venous pressure profiles based on a series of sensed and programmed inputs and the current state.

Description of the States:

Five states are illustrated in (FIG. 17):

(a) A STATIC state (1701)—which represents time spent in a fixed posture, where the sensed vertical height doesn't change. This state keeps track of the time spent in a given stable posture and, upon exiting the state, logs the pressure data. This state corresponds to the steady state phase of the venous pressure waveforms of FIG. 7 and FIG. 9.

(b) An ACTIVITY CHECK state (1702)—this represents a transition state where some initial stepping activity has been detected. This state checks to see if a predefined number of steps 'NI' in a predefined time interval have been taken and determines whether or not the individual wearing the sensor is walking or merely taking a short number of steps. This state corresponds to the transition from any state to the Leg Activity stage of the waveform of FIG. 9.

(c) An ACTIVITY state (1703)—this state tracks the number of steps and time between steps taken by the wearer. The states then determine the reduction in venous pressure due to walking based on the degree of CVI, number of steps taken and the estimated walking speed of the individual, (based on normative values from Kugler 2001). The program exits the ACTIVITY state when an INACTIVITY interrupt is detected. One example of an inactivity interrupt trigger could be a lack of a significant change in a sensed input over a specified time frame, representing a lack of movement. This state corresponds to the Leg Activity stage of the waveform of FIG. 9.

(d) A TRANSITION DOWN state (1704)—this state which tracks changes in venous pressure based on a drop in vertical height or venous pressure. This state corresponds to the phase after the postural change 2 outlined in FIG. 7, where the venous pressure is decreasing.

(e) A REFILL state (1705)—this state creates a venous pressure profile corresponding to an increase in venous pressure due to an increase in vertical height or cessation of activity. This state corresponds to the transition phase of the waveforms of FIG. 7 and FIG. 9.

Description of the Signals:

The state machine is driven by the following inputs which may be sensed, calculated or programmed:

Hv—Vertical Height between the ankle and the heart.

Steps—number of steps detected by one of the kinematic sensors or other means.

INACT—inactivity interrupt indicating a lack of activity within a predefined time period.

ACT—activity interrupt indicating a stepping motion based on a sensed input.

Pr—Current Pressure as determined by the hydrostatic pressure equation and the Sensed vertical Height, Hv EPr—estimated stable venous pressure at the end of a refill period.

For the purposes of data logging of venous pressure profiles, each state keeps track of the venous pressure profile within that state, and saves the data to memory upon exiting the state. This allows the venous pressure profile to be read and illustrated using the data saved to memory.

Description of the State Transitions:

There are 19 possible transitions between the 5 states, and these are described in terms of the source state from which they exit:

STATIC State Output Transitions:

STATIC to ACTIVITY CHECK (1716): if the state machine is in the STATIC state and an activity interrupt indicating a stepping motion is detected the program logs the pressure profile for the STATIC state moves to the ACTIVITY CHECK state.

STATIC to STATIC (1706): if the state machine is in the STATIC state and no activity interrupt or no-change in vertical height (Hv) is detected, the program remains in the STATIC state and updates the time associated with the current posture.

STATIC to TRANSITION DOWN (1721): if the state machine is in the STATIC state and no activity interrupt but a decrease in vertical height (Hv) is detected, the program logs the pressure profile for the STATIC state moves to the TRANSITION DOWN (pressure-decreasing) state.

STATIC to REFILL (1722): if the state machine is in the STATIC state and no activity interrupt but an increase in vertical height (Hy) is detected, the program logs the pressure profile for the STATIC state moves to the REFILL state.

ACTIVITY CHECK State Output Transitions:

ACTIVITY CHECK to STATIC (1707): if the state machine is in the ACTIVITY CHECK state and the number of steps detected in the ACTIVITY CHECK state is less than 'N' steps, and the vertical height, Hv, hasn't changed from the previous state then the program logs the pressure profile for the ACTIVITY CHECK state and moves to the STATIC state.

ACTIVITY CHECK to TRANSITION DOWN (1718): if the state machine is in the ACTIVITY CHECK state and the number of steps detected in the ACTIVITY CHECK state is less than 'N' steps, and the vertical height, Hv, is less than the vertical height from the previous state then the program logs the pressure profile for the ACTIVITY CHECK state and moves to the TRANSITION DOWN state.

ACTIVITY CHECK to REFILL (1724): if the state machine is in the ACTIVITY CHECK state and the number of steps detected in the ACTIVITY CHECK state is less than 'N' steps, and the vertical height, Hv, is greater than the vertical height from the previous state then the program logs the pressure profile for the ACTIVITY CHECK state and moves to the REFILL state.

ACTIVITY CHECK to ACTIVITY (1708): if the state machine is in the ACTIVITY CHECK state and the number of steps detected in the ACTIVITY CHECK state is greater than 'N' steps, and the vertical height then the program logs the pressure profile for the ACTIVITY CHECK state and moves to the ACTIVITY state.

ACTIVITY State Output Transitions:

ACTIVITY to ACTIVITY (1709): If no inactivity interrupt (INACT) is detected, the program stays in the ACTIVITY state.

ACTIVITY to TRANSITION DOWN (1710): if the state machine is in the ACTIVITY state and an inactivity interrupt (INACT) is detected and the vertical height (Hv) is decreasing the program logs the pressure profile for the ACTIVITY state and moves to the TRANSITION down state.

ACTIVITY to REFILL (1711): if the state machine is in the ACTIVITY state and an inactivity interrupt (INACT) is detected and the calculated venous pressure at the end of the ACTIVITY state (Pr) is less than the Estimated venous pressure (EPr) corresponding to the current vertical height under static conditions then the program logs the pressure profile for the ACTIVITY state and moves to the REFILL state.

TRANSITION DOWN State Output Transitions:

TRANSITION DOWN to TRANSITION DOWN (1712): If no activity interrupt (ACT) is detected, and the vertical height (Hv) continues to decrease the program stays in the TRANSITION DOWN state.

TRANSITION DOWN to REFILL (1720): if the state machine is in the TRANSITIONDOWN state and no activity interrupt (ACT) is detected and the vertical height (Hv) is increasing, the program logs the pressure profile for the TRANSITION DOWN state and moves to the REFILL state.

TRANSITION DOWN to STATIC (1717): if the state machine is in the TRANSITION DOWN and no activity interrupt (ACT) is detected and the vertical height (Hv) is not changing, the program logs the pressure profile for the TRANSITION DOWN state and moves to the STATIC state.

TRANSITION DOWN to ACTIVITY CHECK (1719): if the state machine is in the TRANSITION DOWN and an activity interrupt (ACT) is detected the program logs the pressure profile for the TRANSITION DOWN state and moves to the ACTIVITY CHECK state.

REFILL State Output Transitions:

REFILL to TRANSITION DOWN (1713): If no activity interrupt (ACT) is detected, and the vertical height (Hv) is decreasing the program the program logs the pressure profile for the REFILL state and moves to the TRANSITION DOWN state.

REFILL to REFILL (1714): if the state machine is in the REFILL state and no activity interrupt (ACT) is detected and the vertical height (Hv) is increasing or the current calculated pressure (Pr) is not equal to the estimated pressure (EPr) for the current vertical height (Hv), the program stays in the REFILL state.

REFILL to STATIC (1723): if the state machine is in the REFILL and no activity interrupt (ACT) is detected and the vertical height (Hv) is not changing, the program logs the pressure profile for the REFILL state and moves to the STATIC state.

REFILL to ACTIVITY CHECK (1715): if the state machine is in the REFILL and an activity interrupt (ACT) is detected the program logs the pressure profile for the REFILL state and moves to the ACTIVITY CHECK state.

It will be appreciated that the system of the invention can continuously calculate the vertical height between the heart and the ankle in order to estimate a specific physiological parameter, the ankle venous pressure, which is of clinical use in understanding chronic venous insufficiency. The pressure algorithms accommodate two different types of venous pressure estimates: those observed during a static posture, and those observed during a change in posture of during walking.

Venous pressure measurement has previously only been possible using invasive pressure measurement techniques using a large needle which is only reliable over a short treatment period. The invention, however, allows continuous non-invasive estimation of venous pressure.

The invention is not limited to the embodiments described but may be varied in construction and detail.

The invention claimed is:

1. A monitoring system comprising:
    a plurality of sensors adapted to be worn by a user and to provide sensor data;
    the plurality of sensors selected from accelerometers measuring limb segment tilt and rapid changes to acceleration caused by impact forces during impact of user's heel during stepping and walking, ultrasound range detectors measuring knee angle and time rate of change of knee angle, piezoelectric sensors measuring change in height and time rate of change of the change in height, gyroscopes measuring limb angular velocity and time rate of change of the limb angular velocity, magnetometers measuring body segment tilt and time rate of change of the body segment tilt, foot switches measuring heel input events during stepping and walking and time rate of change of the heel input events, or smart textiles incorporating electrical sensing elements detecting step counts, postural transitions, walking, lying, sitting, or standing up and/or measuring step counts;
    an output device; and
    a processor linked with the plurality of sensors to receive and process sensor data, and said processor is configured to:
    estimate user step rate in real-time as being indicative of rate of calf muscle activity in real-time;
    use said step rate to determine if the person is static, or active, or in a transition between static and active;
    operate as a finite state machine to define states including:
        a user static state, representing time spent in a fixed posture in which sensed user vertical height as measured by the plurality of sensors does not change, said fixed postures including lying, sitting and standing postures as measured by the plurality of sensors,
        a user activity state as measured by the plurality of sensors, representing time spent taking steps, a refill state for a transition phase of pressure increasing due to increase in user height or cessation of activity as measured by the plurality of sensors, during which a user's veins fill,
        a transition down state for venous pressure decreasing due to drop in vertical height arising from a posture change or start of user motive activity as measured by the plurality of sensors, during which the start of pumping action of the calf muscle begins lowering venous pressure to a depressed value during a plateau phase, and
        a user motive activity check state as measured by the plurality of sensors for checking for user activity;
    generate an inactivity interrupt to trigger exit from the activity state;
    generate an activity interrupt to trigger transition to the activity check state;
    store a refill time for a patient by either (a) receiving said refill time as an input setting, or (b) selecting said refill time from pre-set values for degree of chronic venous insufficiency CVI, or (c) determining said refill time using indirect measurement of venous haemodynamics using air-plethysmography, and to use said stored refill time in the finite state machine to estimate a transition time of the venous pressure increasing due to an increase in user height or a cessation of user motive activity as measured by the plurality of sensors, during which a user's veins fill;
    identify lower leg activity primary phases as measured by the plurality of sensors including an emptying phase, and a plateau phase in which the veins do not empty any further and active venous pressure is maintained at a depressed level, and to determine a value for mean slope of active venous pressure change in the emptying phase by a rate of muscle activation and ankle range of motion as measured by the plurality of sensors, and to determine minimal pressure in the plateau phase by said degree of chronic venous insufficiency, a value for user calf circumference, and values for user ankle range of motion and head change as measured by the plurality of sensors;
    generate in real time an estimate of static venous pressure of a user while the user is static, without calf muscle pump activity as measured by the plurality of sensors, by calculating a vertical distance $\Delta h$ between a level of the user's heart and ankle, by:
        determining a first joint angle made by a thigh of the user with a first reference axis as measured by the plurality of sensors, determining a second joint angle made by of a lower leg of the user with a second reference axis, calculating $\Delta h$ using a value for length of the thigh, a value for length of the shank of the leg, a value for distance from the hip to the level of the heart, and the first joint angle and the second joint angle using determined postural data, and completing said estimation of static venous pressure by an equation in which static pressure=$\rho g \Delta h$, in which $\rho$ is blood density, g is acceleration due to gravity, and $\Delta h$ is said vertical distance between the user's heart and ankle; and
    generate an estimate of user active venous pressure according to said static venous pressure estimate, and a reduction in venous pressure from said static venous pressure estimate, said reduction being determined by a rate of calf muscle activity, and a value for degree of user chronic venous insufficiency;
    actuate said output device to provide real time user feedback including at least one of auditory, visual or tactile alerts, said feedback including one or more of:
        an alert if a pre-determined postural or activity threshold has been exceeded,
        an alert if a venous pressure level is exceeded,
        an alert according to estimated venous pressure arising from posture status such as prolonged periods of inactivity,
        feedback to assist with alleviating venous pooling or elevation of venous pressure for prevention and treatment of CVI, including promotion of activities including exercises which activate the lower leg muscles and hence reduce venous pressure, and limiting of postures which predispose a user to sustained elevated venous pressure, real time feedback of average venous pressure levels over time intervals, and to indicate an assessment of user adherence to prescribed activities including lower leg elevation and to goals for reduction of average venous pressure; and communicate the venous pressure estimates and user feedback to one or more devices; and a neuromuscular electrical stimulation device, said processor being configured to activate said neuromuscular electrical stimulation device according to said user feedback.

2. The monitoring system as claimed in claim 1, wherein the plurality of sensors are adapted to measure the acceleration and/or tilt of a limb segment in one or more axes.

3. The monitoring system as claimed in claim 1, wherein the system includes a pressure transducer adapted to detect status of a dressing, and wherein the processor is adapted to use an input from said pressure transducer as a conditional input for said estimation of venous pressure.

4. The monitoring system as claimed in claim 1, wherein the processor is configured to determine or select neuromuscular electrical stimulation device parameters according to at least one of: a venous pressure estimate, average venous pressure over time intervals, a venous pressure-time integral, physical activity levels, leg elevation levels, and neuromuscular electrical stimulation device usage statistics.

5. The monitoring system as claimed in claim 1, wherein the processor is configured to generate or select neuromuscular electrical stimulation device stimulation parameters including at least one of: stimulation amplitude; pulse width, pulse frequency; stimulation envelope ramp-up, ramp-down, on and off times; number of channels and stimulation schedule.

6. The monitoring system as claimed in claim 1, wherein the processor is configured to execute a state machine algorithm in which:

if in the static state and an activity interrupt indicating a stepping motion is detected the processor logs a venous pressure profile for the static state and moves from the static state to the activity check state, if in the static state and no activity interrupt or no change in vertical height is detected as measured by the plurality of sensors, the processor remains in the static state and the processor updates a time associated with the current posture, if in the static state and there is no activity interrupt but a decrease in vertical height is detected as measured by the plurality of sensors, the processor logs a venous pressure profile for the static state and moves from the static state to the transition down state, and if in the static state and there is no activity interrupt but an increase in vertical height is detected as measured by the plurality of sensors, the processor logs a pressure profile for the static state and moves to the refill state.

7. The monitoring system as claimed in claim 1, wherein the processor is configured to execute a state machine algorithm in which:

if in the activity state and the number of steps detected in the activity state is less than a predetermined number of steps, and the vertical height Hv has not changed from the previous state then the processor logs a venous pressure profile for the activity state and moves to the static state, if in the activity check state and the number of steps detected in the activity check state is less than a predetermined number of steps, and the vertical height Hv is less than the vertical height from the previous state then the processor logs a pressure profile for the activity check state and moves to the transition down state, if in the activity check state and the number of steps detected in the activity check state is less than a predetermined number of steps, and the vertical height Hv is greater than the vertical height from the previous state, then the processor logs the pressure profile for the activity check state and moves to the refill state, if in the activity check state and the number of steps detected in the activity check state is greater than a predetermined number of steps, then the processor logs the pressure profile for the activity check state and moves to the activity state, if no inactivity interrupt is detected, the processor stays in the activity state, if in the activity state and an inactivity interrupt is detected and the vertical height Hv is decreasing the processor logs the pressure profile for the activity state and moves to the transition down state, if in the activity state and an inactivity interrupt is detected and a calculated venous pressure Pr at the end of the activity state is less than an estimated venous pressure corresponding to the current vertical height under static conditions then the processor logs the pressure profile for the activity state and moves to the refill state, and if no activity interrupt is detected, and the vertical height Hv continues to decrease the processor stays in the transition down state.

8. The monitoring system as claimed in claim 1, wherein the processor is configured to execute a state machine algorithm in which:

if in the transition down state and no activity interrupt is detected and the vertical height Hv is increasing, the processor logs a pressure profile for the transition down state and moves to the refill state, if in the transition down state and no activity interrupt is detected and the vertical height Hv is not changing, log a pressure profile for the transition down state and move to the static state, if in the transition down state and an activity interrupt is detected the processor logs the pressure profile for the transition down state and moves to the activity check state, if in the refill state and no activity interrupt is detected, and the vertical height Hv is decreasing the processor logs a pressure profile for the refill state and moves to the transition down state, if in the refill state and no activity interrupt is detected and the vertical height Hv is increasing or current estimated venous pressure Pr is not equal to an estimated stable venous pressure EPr for the current vertical height Hv, the processor stays in the refill state, if in the refill state and no activity interrupt is detected and the vertical height Hv is not changing, the processor logs the pressure profile for the refill state and moves to the static state, and if in the refill state and an activity interrupt is detected the processor logs the pressure profile for the refill state and moves to the activity check state.

9. The monitoring system as claimed in claim 1, wherein the processor is configured to process interval time data to determine if a postural change occurred during an interval, and to estimate an average pressure during said interval using estimates of static venous pressures, the duration of the interval, and the venous refill rate, and in which the processor is configured to identify lower leg activity primary phases including an emptying phase, and a plateau phase in which the veins do not empty any further and active venous pressure is maintained at a depressed level, and the processor is configured to determine a value for mean slope of the active venous pressure change in the emptying phase by the rate of muscle activation and ankle range of motion, and to determine minimal pressure in the plateau phase by the degree of chronic venous insufficiency, calf circumference, ankle range of motion and head height change.

10. The monitoring system as claimed in claim 1, wherein the processor determines the reduction in venous pressure due to walking based on the degree of user chronic venous insufficiency, number of steps taken and the estimated walking speed of the individual as measured by the at least one sensor and normative values.

\* \* \* \* \*